(12) United States Patent
Huang et al.

(10) Patent No.: US 12,570,734 B2
(45) Date of Patent: *Mar. 10, 2026

(54) C-TERMINAL ANTI-SCLEROSTIN ANTIBODY VARIANTS

(71) Applicant: AMGEN INC., Thousand Oaks, CA (US)

(72) Inventors: Zhe Huang, Action, MA (US); Jennitte LeAnn Stevens, Thousand Oaks, CA (US); Greg Flynn, Thousand Oaks, CA (US); Szilan Fodor, Thousand Oaks, CA (US); Mark Daris, Thousand Oaks, CA (US)

(73) Assignee: AMGEN INC., Thousand Oaks, CA (US)

( * ) Notice: Subject to any disclaimer, the term of this patent is extended or adjusted under 35 U.S.C. 154(b) by 91 days.

This patent is subject to a terminal disclaimer.

(21) Appl. No.: 18/525,130

(22) Filed: Nov. 30, 2023

(65) Prior Publication Data

US 2024/0352112 A1 Oct. 24, 2024

Related U.S. Application Data

(63) Continuation of application No. 17/934,585, filed on Sep. 23, 2022, now Pat. No. 11,858,983, which is a continuation of application No. 16/971,590, filed as application No. PCT/US2019/024739 on Mar. 29, 2019, now Pat. No. 11,466,079.

(60) Provisional application No. 62/812,741, filed on Mar. 1, 2019, provisional application No. 62/650,762, filed on Mar. 30, 2018.

(51) Int. Cl.
| | |
|---|---|
| *A61K 39/395* | (2006.01) |
| *A61K 47/12* | (2006.01) |
| *A61K 47/26* | (2006.01) |
| *C07K 16/22* | (2006.01) |
| *A61K 39/00* | (2006.01) |

(52) U.S. Cl.
CPC .............. *C07K 16/22* (2013.01); *A61K 47/12* (2013.01); *A61K 47/26* (2013.01); *A61K 2039/505* (2013.01); *C07K 2317/24* (2013.01)

(58) Field of Classification Search
None
See application file for complete search history.

(56) References Cited

U.S. PATENT DOCUMENTS

| | | |
|---|---|---|
| 4,331,647 A | 5/1982 | Goldenberg |
| 4,376,110 A | 3/1983 | David et al. |
| 4,411,993 A | 10/1983 | Gillis |
| 4,427,115 A | 1/1984 | Laipply |
| 4,543,439 A | 9/1985 | Frackelton et al. |
| RE32,011 E | 10/1985 | Zimmerman et al. |
| 4,837,440 A | 6/1989 | Burtscher et al. |
| 4,902,614 A | 2/1990 | Wakabayashi et al. |
| 5,070,108 A | 12/1991 | Margolis |
| 5,145,684 A | 9/1992 | Liversidge et al. |
| 5,223,409 A | 6/1993 | Ladner et al. |
| 5,399,363 A | 3/1995 | Liversidge et al. |
| 5,453,492 A | 9/1995 | Buetzow et al. |
| 5,466,468 A | 11/1995 | Schneider et al. |
| 5,543,158 A | 8/1996 | Gref et al. |
| 5,552,157 A | 9/1996 | Yagi et al. |
| 5,565,213 A | 10/1996 | Nakamori et al. |
| 5,567,434 A | 10/1996 | Szoka, Jr. |
| 5,571,714 A | 11/1996 | Dasch et al. |
| 5,627,052 A | 5/1997 | Schrader |
| 5,641,515 A | 6/1997 | Ramtoola |
| 5,698,426 A | 12/1997 | Huse |
| 5,738,868 A | 4/1998 | Shinkarenko |
| 5,780,263 A | 7/1998 | Hastings et al. |
| 5,795,587 A | 8/1998 | Gao et al. |
| 5,795,965 A | 8/1998 | Tsuchiya et al. |
| 5,811,238 A | 9/1998 | Stemmer et al. |
| 5,830,721 A | 11/1998 | Stemmer et al. |
| 5,837,458 A | 11/1998 | Minshull et al. |
| 5,877,397 A | 3/1999 | Lonberg et al. |
| 6,054,561 A | 4/2000 | Ring et al. |
| 6,057,421 A | 5/2000 | Muller et al. |
| 6,117,911 A | 9/2000 | Grainger et al. |
| 6,133,426 A | 10/2000 | Gonzalez et al. |
| 6,180,370 B1 | 1/2001 | Queen et al. |
| 6,207,153 B1 | 3/2001 | Dan et al. |
| 6,395,511 B1 | 5/2002 | Brunkow et al. |
| 6,489,445 B1 | 12/2002 | Brunkow et al. |
| 6,495,736 B1 | 12/2002 | Brunkow et al. |
| 6,703,199 B1 | 3/2004 | Koide |
| 6,803,453 B1 | 10/2004 | Brunkow et al. |
| 6,806,055 B2 | 10/2004 | Berman et al. |
| 6,815,201 B2 | 11/2004 | Pinter |

(Continued)

FOREIGN PATENT DOCUMENTS

| | | |
|---|---|---|
| JP | 04-141095 A | 5/1992 |
| JP | 2010-536396 A | 12/2010 |

(Continued)

OTHER PUBLICATIONS

A diagram of a relevant part of the human genome (064), citation in Appeal, European Patent No. 1133558, dated Apr. 15, 2010.

(Continued)

*Primary Examiner* — Christine J Saoud

(74) *Attorney, Agent, or Firm* — MARSHALL, GERSTEIN & BORUN LLP

(57) ABSTRACT

The invention generally relates to anti-sclerostin antibodies having C-terminal modifications, and compositions comprising such antibodies.

19 Claims, 3 Drawing Sheets

Specification includes a Sequence Listing.

(56) References Cited

U.S. PATENT DOCUMENTS

| | | | |
|---|---|---|---|
| 6,818,748 | B2 | 11/2004 | Fulton et al. |
| 7,192,583 | B2 | 3/2007 | Brunkow et al. |
| 7,226,902 | B2 | 6/2007 | Winkler et al. |
| 7,381,409 | B2 | 6/2008 | Winkler et al. |
| 7,572,899 | B2 | 8/2009 | Brunkow et al. |
| 7,578,999 | B2 | 8/2009 | Winkler et al. |
| 7,592,429 | B2 | 9/2009 | Paszty et al. |
| 7,642,238 | B2 | 1/2010 | Shaughnessy |
| 7,758,858 | B2 | 7/2010 | Brunkow et al. |
| 7,868,134 | B2 | 1/2011 | Winkler et al. |
| 7,872,106 | B2 | 1/2011 | Paszty et al. |
| 8,178,099 | B2 | 5/2012 | Ellies |
| 8,383,801 | B2 | 2/2013 | Paszty |
| 8,563,271 | B2 | 10/2013 | Winkler et al. |
| 8,637,643 | B2 | 1/2014 | Latham et al. |
| 8,715,663 | B2 | 5/2014 | Paszty et al. |
| 8,992,911 | B2 | 3/2015 | Winkler et al. |
| 9,011,856 | B2 | 4/2015 | Winkler et al. |
| 9,296,812 | B2 | 3/2016 | Paszty |
| 9,353,174 | B2 | 5/2016 | Paszty et al. |
| 11,466,079 | B2 | 10/2022 | Huang et al. |
| 2003/0165410 | A1 | 9/2003 | Taylor |
| 2003/0166247 | A1 | 9/2003 | Brunkow et al. |
| 2003/0186915 | A1 | 10/2003 | Pan et al. |
| 2003/0229041 | A1 | 12/2003 | Sutherland et al. |
| 2004/0009535 | A1 | 1/2004 | Brunkow et al. |
| 2004/0023356 | A1 | 2/2004 | Krumlauf et al. |
| 2004/0058321 | A1 | 3/2004 | Brunkow et al. |
| 2004/0141875 | A1 | 7/2004 | Doshi |
| 2004/0146888 | A1 | 7/2004 | Paszty et al. |
| 2004/0158045 | A1 | 8/2004 | Brunkow et al. |
| 2005/0014650 | A1 | 1/2005 | Seitz et al. |
| 2005/0085418 | A1 | 4/2005 | Winkler et al. |
| 2005/0106683 | A1 | 5/2005 | Winkler et al. |
| 2005/0238646 | A1 | 10/2005 | Ledbetter et al. |
| 2006/0233801 | A1 | 10/2006 | Brunkow et al. |
| 2007/0072797 | A1 | 3/2007 | Robinson et al. |
| 2007/0110747 | A1 | 5/2007 | Paszty et al. |
| 2007/0148774 | A1 | 6/2007 | Mccafferty et al. |
| 2007/0292444 | A1 | 12/2007 | Krumlauf et al. |
| 2008/0182788 | A1 | 7/2008 | Brunkow et al. |
| 2008/0234219 | A1 | 9/2008 | Brunkow et al. |
| 2009/0074763 | A1 | 3/2009 | Padhi et al. |
| 2009/0117118 | A1 | 5/2009 | Winkler et al. |
| 2009/0304713 | A1 | 12/2009 | Paszty et al. |
| 2010/0015665 | A1 | 1/2010 | Latham et al. |
| 2010/0036091 | A1 | 2/2010 | Robinson et al. |
| 2010/0151524 | A1 | 6/2010 | Winkler et al. |
| 2010/0297697 | A1 | 11/2010 | Ambrosius et al. |
| 2011/0044978 | A1 | 2/2011 | Ke |
| 2011/0097342 | A1 | 4/2011 | Paszty et al. |
| 2011/0150866 | A1 | 6/2011 | Brunkow et al. |
| 2014/0271626 | A1 | 9/2014 | Chumsae et al. |
| 2020/0131253 | A1 | 4/2020 | Parren et al. |

FOREIGN PATENT DOCUMENTS

| | | | |
|---|---|---|---|
| JP | 2014-526884 | A | 10/2014 |
| WO | 91/13152 | A1 | 9/1991 |
| WO | 92/01047 | A1 | 1/1992 |
| WO | 92/02551 | A1 | 2/1992 |
| WO | 92/06693 | A1 | 4/1992 |
| WO | 95/30003 | A2 | 11/1995 |
| WO | 96/04375 | A1 | 2/1996 |
| WO | 98/21335 | A1 | 5/1998 |
| WO | 99/03996 | A1 | 1/1999 |
| WO | 99/06554 | A2 | 2/1999 |
| WO | 99/15556 | A1 | 4/1999 |
| WO | 00/32773 | A1 | 6/2000 |
| WO | 00/44777 | A1 | 8/2000 |
| WO | 00/75317 | A2 | 12/2000 |
| WO | 01/64885 | A1 | 9/2001 |
| WO | 01/92308 | A2 | 12/2001 |
| WO | 01/98491 | A2 | 12/2001 |
| WO | 02/24888 | A2 | 3/2002 |
| WO | 02/30463 | A2 | 4/2002 |
| WO | 03/50513 | A2 | 6/2003 |
| WO | 03/87763 | A2 | 10/2003 |
| WO | 2003/106657 | A2 | 12/2003 |
| WO | 2004/082608 | A2 | 9/2004 |
| WO | 2004/094477 | A1 | 11/2004 |
| WO | 2004/098491 | A2 | 11/2004 |
| WO | 2005/003158 | A2 | 1/2005 |
| WO | 2005/014650 | A2 | 2/2005 |
| WO | 2005/115356 | A2 | 12/2005 |
| WO | 2006/015373 | A2 | 2/2006 |
| WO | 2006/065746 | A2 | 6/2006 |
| WO | 2006/102070 | A2 | 9/2006 |
| WO | 2006/119062 | A2 | 11/2006 |
| WO | 2006/119107 | A2 | 11/2006 |
| WO | 2007/080129 | A1 | 7/2007 |
| WO | 2008/061013 | A2 | 5/2008 |
| WO | 2008/092894 | A1 | 8/2008 |
| WO | 2008/115732 | A2 | 9/2008 |
| WO | 2008/133722 | A2 | 11/2008 |
| WO | 2009/026558 | A1 | 2/2009 |
| WO | 2009/039175 | A2 | 3/2009 |
| WO | 2009/047356 | A1 | 4/2009 |
| WO | 2009/056634 | A2 | 5/2009 |
| WO | 2009/079471 | A1 | 6/2009 |
| WO | 2009/131553 | A2 | 10/2009 |
| WO | 2009/149189 | A2 | 12/2009 |
| WO | 2010/100179 | A2 | 9/2010 |
| WO | 2010/100200 | A2 | 9/2010 |
| WO | 2010/115932 | A1 | 10/2010 |
| WO | 2010/130830 | A2 | 11/2010 |
| WO | 2011/143307 | A1 | 11/2011 |
| WO | 2012/028683 | A1 | 3/2012 |
| WO | 2012/058393 | A2 | 5/2012 |
| WO | 2013/004841 | A1 | 1/2013 |
| WO | 2014/159579 | A1 | 10/2014 |
| WO | 2017/153541 | A1 | 9/2017 |
| WO | 2018/115880 | A1 | 6/2018 |

OTHER PUBLICATIONS

Abbas et. al., (Eds.), Cellular and Molecular Immunology, Third Edition, Section II, p. 54 (1997).

Alberts et. al. (Eds.), Molecular Biology of the Cell, Third Edition, Chapter 23, p. 1212 (1994).

Albertsen et. al., A physical map and candidate genes in the BRCA1 region on chromosome 17q12-21. Nat. Genet., 7:472-9 (1994).

Alting-Mees et. al., Monoclonal antibody expression libraries: A rapid alternative to hybridomas. Strat. Malec. Biol., 3:1-9 (1990).

Alves et al., Sclerosteosis: A marker of Dutch ancestry? Rev. Bras. Genet., 4:825-34 (1982).

Andersson et. al., Molecular genetics and pathophysiology of 17ß-hydroxysteriod dehydrogenase 3 deficiency. J. Clin. Endrocrinol. Metab., 81(1): 130-6 (1996).

Angal et al., A single amino acid substitution abolishes the heterogeneity of chimeric mouse/human (IgG4) antibody, Mol. Immunol., 30(1):105-8 (1993).

Annex regarding the purported relevance of gene/peptides mentioned by Professor Arnett, dated Mar. 18, 2011.

Anonymous, Amgen presents denosumab and sclerostin antibody data at American Society for Bone and Mineral Research Annual Meeting. Amgen Media Press Release. <www.amgen.com/media/media_pr_detail.jsp?releaseID=907028> (2006).

Anonymous, UCB on track. UCB News <http://hugin.info/133973/R/1176122/233395.pdf> (2007).

Ardery, Liquid Chromatography—Mass Spectrometry: An Introduction (2003).

Arpino et al., Combined liquid chromatography mass spectrometry Part I. Coupling by means of moving belt interface, Mass Spectrometry Rev. 8:35-55 (1989).

Attana Application Example, cited in Opposition against European Patent No. 1721979 by Opponent: Novartis AG, dated Jun. 15, 2011.

Avsian-Kretchmer et. al., Comparative genomic analysis of the eight-membered ring cystine knot—containing bone morphogenetic protein antagonists. Malec. Endrocrinol., 18(1):1-12 (2004).

(56)         References Cited

OTHER PUBLICATIONS

Babcook et. al., A novel strategy for generating monoclonal antibodies from single, isolated lymphocytes producing antibodies of defined specificities. Proc. Natl. Acad. Sci. USA, 93:7843-8 (1996).
Baines et al., Purification of immunoglobulin G (IgG). Meth. Malec. Biol., 10:79-104 (1992).
Balemans et al., Extracellular regulation of BMP signaling in vertebrates: A cocktail of modulators. Dev. Biol., 250:231-50 (2002).
Balemans et al., Localization of the gene for sclerosteosis to the van Buchem disease-gene region on chromosome 17q12-q21. Am. J. Hum. Genet., 64:1661-9 (1999).
Balemans et. al., Increased bone density in sclerosteosis is due to the deficiency of a novel secreted protein (SOST). Hum. Mol. Genet., 10:537-43 (2001).
Balint et al., Antibody engineering by parsimonious mutagenesis. Gene, 137(1):109-18 (1993).
Bateman et. al., Granulins: The structure and function of an emerging family of growth factors. J. Endocrinol., 158:145-51 (1998).
Baxevanis (Ed.) et al., Bioinformatics: A practical guide to the analysis of genes and proteins, John Wiley & Sons, Inc. paqe 234 (1998).
Bee et al., Exploring the Dynamic Range of the Kinetic Exclusion Assay in Characterizing Antigen-Antibody Interactions, PLoS One, (2012).
Beighton et. al., Heterozygous manifestations in the heritable disorders of the skeleton. Pediatr. Radiol., 27: 397-401 (1997).
Beighton et. al., The clinical features of sclerosteosis. Clin. Genet., 25:175-81 (1984).
Beighton et. al., The syndromic status of sclerosteosis and van Buchem disease. Ann. Intern. Med., 84:393-7 (1976).
Bellows et. al., Parathyroid hormone reversibly suppresses the differentiation of osteoprogenitor cells in functional osteoblasts. Endocrinol., 127(6): 3111-6 (1990).
Bendayan, Possibilities of false immunocytochemical results generated by the use of monoclonal antibodies: The example of the anti-proinsulin antibody. J. Histochem. Cytochem., 43(9):881-6 (1995).
Bendig, Humanization of rodent monoclonal antibodies by CDR grafting. Methods, 8:83-93 (1995).
Bergfeld et. al., Release of ATP from human erythrocytes in response to a brief period of hypoxia and hypercapnia. Cardiovascular Res., 26: 40-7 (1992).
Berman et. al., The protein data bank. Acta. Cryst., 58(1):899-907 (2002).
Bigger versions of Figures from Declaration of Professor Teresa Attwood, citation in Appeal, European Patent No. 1133558, dated Apr. 13, 2010.
Bird et al., Single-chain antigen-binding proteins, Science 242: 423-6 (1988).
Birren et. al., EMBL sequence database accession No. AC003098.2, Nov. 14, 1997.
Bishop (Ed.), Guide to Human Genome Computing, Second Edition, Academic Press, Chapter 1: Introduction to human genome computer via the world wide web, pp. 1-14 (2003).
Black et. al., A somatic cell hybrid map of the long arm of human chromosome 17, containing the familial breast cancer llocus (BRCAI). Am. J. Hum. Genet., 52:702-10 (1993).
Blum et al., Study plan for German students in the summer of 1998, University Bioinformatik lecture announcement (1998).
Boden et. al., Glucocorticoid-induced differentiation of fetal rat calvarial osteoblasts is mediated by bone morphogenetic protein-6. Endocrinology, 138(7):2820-8 (1997).
Boerner et. al., Production of antigen-specific human monoclonal antibodies from in vitro-primed human splenocytes. J. Immunol., 147:86-95 (1991).
Bonaldo et al., EMBL Sequence Database Accession No. AI113131, Sep. 4, 1998.
Bonaldo et al., Normalization and subtraction: Two approaches to facilitate gene discovery. Genome Res., 6(9):791-806 (1996).

Bondestam, "Ligands & Signaling Components of the Transforming Growth Factor," Helsinki University Biomedical Dissertations (2002).
Bork et al., Go hunting in sequence databases by watch out for the traps. Trends Genet. 12: 425-7 (1996).
Borrok et al., Revisiting the Role of Glycosylation in the Structure of Human IgG Fe, ACS Chemical Biology, 1596-602 (2012).
Bos et al., ras ongogenes in human cancer: A review, Cancer Res., 49: 4682-9 (1989).
Bost et. al., Antibodies against a peptide sequence within the HIV envelope protein crossreacts with human interleukin-2. Immunol. Invest., 17(6&7):577-86 (1988).
Bostrom et. al., Ligand and signaling components of the transforming growth factor 13 family. J. Orth. Res., 13:357-67 (1995).
Bottcher et. al., NCBI Sequence database accession No. NM_004329, Aug. 2, 2009.
Bouffard et al., A physical map of human chromosome 7: An integrated YAC contig map with average STS spacing of 79 kb. Genome Res., 7: 673-92 (1997).
Notice of Opposition against European Patent No. 1721979, Opponent: Eli Lilly & Company, dated Jun. 15, 2011.
Notice of Opposition against European Patent No. 1721979, Opponent: Laudens, dated Jun. 15, 2011.
Notice of Opposition against European Patent No. 1721979, Opponent: Novartis AG, dated Jun. 15, 2011.
Notice of Opposition against European Patent No. 2556841, dated Feb. 10, 2017.
Notice of Opposition to European Patent No. 1 133 558 dated May 29, 2007.
Nygren et al., Scaffolds for engineering novel binding sites in proteins. Curr. Opin. Struct. Biol. 7: 463-9 (1997).
Observations of Opponent: Laudens in response to summons to oral proceedings in Opposition against European Patent No. 1721979, dated Feb. 25, 2013.
Oelgeschlager et. al., The evolutionarily conserved BMP-binding protein twisted gastrulation promotes BMP signalling. Nature, 405:757-63 (2000).
OMIM #607625, Niemann-pick disease, type C2 (2007).
Ominsky, et al., Sclerostin monoclonal antibody treatment increases bone strength in aged osteopenic ovariectomozed rats. J. Bone Min. Res., 21(1): S44 PRES1161 (2006). Abstract.
Opposition Decision for Opposition against European Patent No. 1721979, dated Aug. 2, 2013.
Opposition Statement of May 20, 2007 filed by Opponent 2 (Eli Lilly) against European Patent No. 1133558.
Oreffo et. al., Human bone marrow osteoprogenitors express estrogen receptor-alpha and bone morphogenetic proteins 2 and 4 mRNA during osteoblastic differentiation. J. Cell. Biochem., 75:382-92 (1999).
Orriss et al., Purinergic signaling and bone remodeling. Curr. Opin. Pharmacol., 10:322-30 (2010).
Oshima et. al., TGF-13 receptor type II deficiency results in defects of yolk Sac hematopoiesis and vasculogenesis. Dev. Biol., 179:297-302 (1996).
Padhi et al., Anti-sclerostin antibody increases markers of bone formation in healthy postmenopausal women. J. Bone Min. Res., 22: S37 (2007).
Padhi et al., OC35—Effects of anti-sclerostin monoclonal antibody in healthy postmenopausal women. Osteoporosis Int., 19: Suppl. 1: S19 (2008).
Padlan et al., Structure of an antibody-antigen complex; Crystal structure of the HyHEL-10 Feb-lysozyme complex. Proc. Natl. Acad. Sci. USA, 86:5938-42 (1989).
Palokangas et. al., Endocytic pathway from the basal plasma membrane to the ruffled border membrane in bone-resorbing osteoclasts. J. Cell Sci., 110: 1767-80 (1997).
Pandey et al., Nucleotide sequence database: A gold mine for biologists. TIBS. 24: 276-80 (1999).
Papapoulos et al., Targeting sclerostin as potential treatment of osteoporosis. Ann. Rheum. Dis., 70(Suppl. 1): 1119-22 (2011).
Patel et. al., Current and potential future drug treatments for osteoporosis. Ann. Rheumatic Dis., 55: 700-14 (1996).
Patentee's Oct. 5, 2012 Submission in EP 2325199.

(56) References Cited

OTHER PUBLICATIONS

Patten et al., Applications of DNA shuffling to pharmaceuticals and vaccines, Curr. Opin. Biotechnol. 8:724-33 (1997).
Pearson et al., Effective protein sequence comparison. Chapter 15, pp. 227-258 (1996).
Piao et al., The proximal promotor region of the gene encoding human 17(beta)-hydroxysteroid dehydrogenase type 1 contains GATA, AP-2, and Sp1 response elements: Analysis of promotor function in choriocarcinoma cells. Endrocrinol., 138(8): 3417-25 (1997).
Piccolo et al., The head inducer Cerberus is a multifunctional antagonist of nodal, BMP and Wnt signals. Nature, 397: 707-10 (1999).
Piek et al., Specificity, diversity, and regulation of TGF-13 superfamily signaling. FASEB J., 13:2105-24 (1999).
Pietromonaco et. al., Protein kinase C-0 phosphorylation of moesin in the actin-binding sequence. J. Biol. Chem., 273:7594-603 (1998).
Pignatti et al., Tracking disease genes by reverse genetics. J. Psychiar. Res., 26(4):287-98 (1992).
Pittenger et. al., Multilineage potential of adult human mesenchymal stem cells. Science, 284: 143-7 (1999).
Pluckthun et al., Expression of functional anitbody Fv and Fab fragments in *Escherichia coli*. Meth. Enzymol., 178:497-515 (1989).
Pockwinse et al., Expression of cell growth and bone specific genes at single cell resolution during development of bone tissue-like organization in primary osteoblast cultures. J. Cell. Biol., 49:310-23 (1992).
Poole et al., Sclerostin is a delayed secreted product of osteocytes that inhibit bone formation. FESEB J. 19: 1842-4 (2005).
Porter, The hydrolysis of rabbit y-globulin and antibodies with crystalline papain. Biochem. J., 73:119-26 (1959).
Proprietor's Response to Opponent's Statement of Grounds of Appeal, European Patent No. 1133558, dated Apr. 15, 2010.
Proprietor's Response to Oppositions against European Patent No. 1721979, UCB Pharma S.A., dated Feb. 20, 2012.
Proprietor's Written submission in preparation for oral proceedings in Opposition against European Patent No. 1721979, Proprietor: UCB Pharma S.A., dated Feb. 25, 2013.
Quintanar-Guerrero et. al., Preparation techniques and mechanisms of formation of biodegradable nanoparticles from preformed polymers. Drua Dev. Ind. Pharm., 24(12):1113-28 (1998).
Rachner et al., Osteoporosis: Now and the future. Lancet, 377(9773): 1276-87 (2011).
Raitt et la., Roitt's Essential Immunology, 9th Edition, pp. 90-91 (1997).
Rawadi et. al., BMP-2 controls alkaline phosphatase expression and osteoblast mineralization by a Wnt autocrine loop. J. Bone Min. Res., 18: 1842-53 (2003).
Reb, Antikorpergegen Sclerostin, Medical Tribune, 39:12 (2007).
Reddi et al., The *Escherichia coli* chaperonin 60 (groEL) is a potent stimulator of osteoclast formation. J. Bone Miner. Res., 13(8): 1260-6 (1998).
Reddi, "Interplay Between Bone Morphogenetic Proteins and Cognate Binding Proteins in Bone and Cartilage Development: Noggin, Chordin and DAN," Arthritis Res., 3(1):1-5 (2000).
Reid, Targeting Sclerostin in Postmenopausal Osteoporosis: Focus on Romosozumab and Blososumab, BioDrugs 31:289-97(2017).
Response to Proprietor's brief of Apr. 15, 2010, European Patent Opposition, EP-1133558 B1, dated Mar. 18, 2011.
Reverberi et al., Factors affecting the antigen-antbody reaction, Blood Transfus, 5:227-240 (2007).
Riggs, "Overview of Osteoporosis," West J. Med., 154:63-77 (1991).
RnD Systems catalogue excerpt, cited in Opposition against European Patent No. 1721979 by Opponent: Novartis AG dated Jun. 15, 2011.
Bowie et al., A method to identify protein sequences that fold into a known three-dimensional structure. Science, 253:164-70 (1991).
Bowie et al., Deciphering the message in protein sequences: Tolerance to amino acid substitutions. Science, 247(4948):1306-10 (1990).

Bradley et al., Modifying the mouse: Design and desire. Bio/Technology, 10:534-9 (1992).
Brandao-Burch et al., Acidosis inhibits bone formation by osteoblasts in vitro by preventing mineralization. Calcit. Tissue Int., 77: 167-74 (2005).
Brenner et al., Population statistics of protein structures: Lessons from structural classifications. Curr. Op. Struct. Biol., 7(3):369-76 (1997).
Brown, Hybridization Analysis of DNA Blots, Current Protocols in Protein Science, 13:A.4H.1-A.4H.9 (1990).
Brown, Hybridization Analysis of DNA Blots, Current Protocols in Protein Science, 2.10.1-2.10.16 (2000).
Bruggemann et al., Production of human antibody repertoires in transgenic mice. Curr. Opin. Biotechnol., 8:455-8 (1997).
Brunkow et. al., Bone dysplasia sclerosteosis results from loss of the SOST gene product, a novel cysteine knot-containing protein. Am. J. Hum. Genet., 68:577-89 (2001).
Burton et al., Human antibodies from combinatorial libraries. Adv. Immunol., 57:191-280 (1994).
Butcher et al., Increased salt concentration reversibly destabilizes p53 quaternary structure and sequence-specific DNA binding. Biochem. J., 298: 513-6 (1994).
Byrne et al., CD4+CD45RBHi T cell transfer induced colitis in mice is accompanied by osteopenia which is treatable with recombinant human osteoprotegerin. Gut, 54:78-86 (2005).
Campbell et al., Totipotency or multipotentiality of cultured cells: Applications and progress. Theriogenology, 47:63-72 (1997).
Carlson et al., Optimizing production of Fc-amidated peptiedes by Chinese hamster ovary cells., BMC Biotechnol., 15(1):95 (2015).
Caverzasio et al., Characteristics and regulation of Pi transport in osteogenic cells for bone metabolism. Kindey Int., 49: 975-80 (1996).
Chan et. al., A new paradigm in the treatment of osteoporosis: Wnt pathway proteins and their antagonists. Curr. Opin. Invest. Drugs, 8:293-8 (2007).
Chandran et. al., Recent trends in drug delivery systems: Liposomal drug delivery system—Preparation and characterization. Indian J. Exp. Biol., 35(8):801-9 (1997).
Charlier et. al., A pore mutation in a novel KOT-like potassium channel gene in an idiopathic epilepsy family. Nat. Genet., 18:53-5 (1998).
Chenu et. al., Glutamate receptors are expressed by bone cells and are involved in bone resorption. Bone, 22(4):295-9 (1998).
Chou et. al., Empirical predication of protein conformation. Ann. Rev. Biochem., 47:251-76 (1979).
Chou et. al., Prediction of the secondary structure of proteins from their amino acid sequence. Adv. Enzvmol. Relat. Areas Mol. Biol., 47:145-8 (1978).
Citation in Opposition Procedure against European Patent No. 2556841. Declaration Under 37 CFR 1.132 (Chris Paszty, Ph. D.) dated Jun. 14, 2012, submitted Jul. 25, 2017.
Clark, Antibody humanization: A case of the 'Emperor's New Clothes' ?. Immunology Today, 21(8):397-402 (2000).
Cogan et. al., NCBI Sequence Database Accession No. NM_033346, Jul. 19, 2005.
Collins, Identifying human disease genes by positional cloning. The Harvey Lectures, Series 86:149-64 (1992).
Collins, Positional cloning moves from perditional to traditional. Nat. Genet., 9:347-50 (1995).
Colman, Effects of amino acid sequence changes on antibody-antigen interactions. Biomolec.Res. Inst., 55:33-6 (1994).
Communication from the European Patent Office providing an "Observation by a Third Party according to Article 115 EPC" submitted in connection with the Opposition to European Patent No. 1 133 558, dated Dec. 3, 2008.
Cook et. al., Structural basis for a functional antagonist in the transforming growth factor 13 superfamily. J. Biol. Chem., 280(48):40177-86 (2005).
Minutes of the first instance of OD oral proceeding dated Mar. 5, 2018.
Cormier, Markers of bone metabolism. Curr. Opin. in Rheu., 7:243-8 (1995).

(56)             References Cited

OTHER PUBLICATIONS

Couvreur et. al., Polyalkylcyanoacrylates as colloidal drug carriers. Grit. Rev. Ther. Drug Carrier Syst., 5(1):1-20 (1988).

Craig et al., Sclerostin binds and regulates the activity of cysteine rich protein 61. Biochem. Biophys. Res. Commun., 293(1): 36-40 (2010).

Craig et. al., Sclerostin-erbB-3 interactions: Modulation of erbB-3 activity by sclerostin. Biochem. Biophys. Res. Commun., 402: 421-4 (2010).

Crameri et. al., DNA shuffling of a family of genes from diverse species accelerates directed evolution. Nature, 391:288-91 (1998).

Dall'Acqua et al., "Antibody Humanization by Framework Shuffling," Methods, 36(1):43-60 (2005).

Davies, et al., Affinity improvement of single antibody VH domains: Residues in all three hypervariable regions affect antigen binding. Immunotechnology, 2(3): 169-79 (1996).

De Jong et al., Evolution of the a-crystallin/small heat-shock protein family. Mol. Biol. Evol., 10(1): 103-26 (1993).

Dean et. al., Matrix vesicles produced by osteoblast-like cells in culture become significantly enriched in proteoglycan-degrading metalloproteinases after addition of 13-glycerophosphate and ascorbic acid. Calcit. Tissue, 54: 399-408 (1994).

Declaration filed in connection with the European Patent EP 1133558 Opposition, Expert opinion of Dr. Auristela Freire de Paes Alves, Ph.D., dated Sep. 9, 2009.

Declaration filed in connection with the European Patent EP 1133558 Opposition, Expert opinion of Dr. Walter Sebald, dated Sep. 24, 2009.

Declaration filed in connection with the European Patent EP 1133558 Opposition, Expert opinion of Prof. Dr. Edaar Winaender, dated Sep. 24, 2009.

Declaration filed in connection with the European Patent EP 1133558 Opposition, Expert opinion of Prof. Dr. Thomas Muller, dated Sep. 23, 2009.

Declaration of Alistair J. Henry, citation in Appeal, European Patent No. 1133558, dated Apr. 2, 2010.

Declaration of Dr. Martyn Robinson, submitted in Opposition to European Patent No. 1133558, dated Jan. 13, 2008.

Declaration of Dr. Mary E. Brunkow, submitted in Opposition to European Patent No. 1133558, dated Jan. 9, 2008.

Declaration of Dr. Paszty dated Nov. 21, 2017.

Declaration of Dr. Raymond Dalgleish dated Dec. 8, 2011, citation in Appeal, European Patent No. 1133558.

Declaration of Dr. Robinson dated Jan. 5, 2015.

Declaration of Prof. Edgar Wingender filed in connection with that Opposition regarding European Patent EP 1133558 B1, dated Mar. 10, 2011.

Lasic, Novel applications of liposomes. Trends Biotechnol., 16(7):307-21 (1998).

Latham, The biochemical and cellular characterization of sclerostin, The causative gene for sclerostenosis. Calcified Tissue International, 70(4):244 (2002).

Lee and Kerns, LS/MS Applications in Drug Development, Mass Spectrometry Reviews, 18:187-279 (1999).

Iemura et al., Direct binding of follistatin to a complex of bone-morphogenetic protein and its receptor inhibits ventral and epidermal cell fates in early Xenopus embryo. Proc. Natl. Acad. Sci. USA, 95:9337-42 (1998).

Leppert et al., Benign familial neonatal epilepsy with mutations in two potassium channel genes. Curr. Opin. Neural., 12: 143-7 (1999).

Lewiecki et al., Sclerostin monoclonal antibody therapy with AMG 785: A potential treatment for osteoporosis. Exp. Opin. Biol. Ther., 11(1): 117-27 (2011).

Li et al., Sclerostin binds to LRP5/6 and antagonizes canonical Wnt signaling. J. Biol. Chem., 280: 19883-7 (2005).

Li et al., Treatment with an anti-sclerostin antibody directly stimulates bone formation in a dose-dependent manner in ovariectomized rats with established osteopenia. J. Bone Min. Res., 22(Suppl. S1): S65 (2007).

Lian et al., Bone Formation: Osteoblast Lineage Cells, Growth Factors, Matrix Proteins, and the Mineralization Process, Primer on the Metabolic Bone Diseases and Disorders of Mineral Metabolism, 4th Edition, 14-29 (1999).

Lierop et al., Van Buchem disease: Clinical, biochemical and densitometric features of patients and disease carriers. J. Bone Miner. Res. Accepted Article (2012).

Liu et al., GenBank Sequence Database Accession No. U25110, Feb. 2, 1996.

Liu et al., Human type II receptor for bone morphogenic proteins (BMPs): Extension of the two-kinase receptor model to the BMPs. Malec. Cell. Biol., 15(7):3479-86 (1995).

Lonberg et. al., Antigen-specific human antibodies from mice comprising four distinct genetic modifications. Nature, 368:856 (1994).

Loots et. al., Genomic deletion of a long-range bone enhancer misregulates sclerostin in Van Buchem disease. Genome Res., 15: 928-35 (2005).

Low et al., Mimicking somatic hypermutation: Affinity maturation of antibodies displayed on bacteriophage using a bacterial mutator strain. J. Mol. Biol., 250:350-68 (1996).

Lowik et al., Wnt signaling is involved in the inhibitory action of sclerostin on BMP-stimulated bone formation. J. Musculoskeleton Neuronal Interact. 6: 357 (2006).

Luckman et al., Heterocycle-containing bisphosphonates cause apoptosis and inhibit bone resorption by preventing protein prenylation: Evidence from structure-activity relationships in J774 macrophages. J. Bone Miner. Res., 13(11):1668-78 (1998).

Luckman et al., Nitrogen-containing bisphosphonates inhibit the mevalonate pathway and prevent post-translational prenylation of GTP-binding proteins, including Ras. J. Bone Miner. Res., 13(4): 581-9 (1998).

Malone et al., Bone anabolism achieved by reducing sclerostin bioavailability with an anti-sclerostin antibody. 37th International Sun Valley Workshop on Skeletal Tissue Biology. Aug. 5-8, 2007.

Mango et al., Carboxy-terminal truncation activates glp-1 protein to specify vulval fates in Caenorhabditis elegans. Lett. Nature, 352: 811-15 (1991).

Margalit et al., Comparative analysis of structurally defined herparin binding sequences reveals a distinct spatial distribution of basic residues. J. Biol. Chem., 268 (26): 19228-31 (1993).

Margalit, Liposome-mediated drug targeting in topical and regional therapies. Grit. Rev. Ther. Drug Carrier Syst., 12(2-3):233-61 (1995).

Marks et. al., By-passing immunization: Building high affinity human antibodies by chain shuffling. Bio/Technology, 10:779-83 (1992).

Matthews et al., Adenovirus protein-protein interactions: Hexon and protein VI. J. Gen. Viral., 75: 3365-74 (1994).

Mayer et. al., Differentiation of osteogenetic cells: Systems and regulators, Z. Orthop., 130: 276-84 (1992)—Abstract Only.

McClung et. al., Inhibition of sclerostin with AMG 785 in post-menopausal women with low bone mineral density: Phase 2 trial results—Abstract presented at the 2012 meeting of the American Society for Bone and Mineral Reasearch (2012).

Memorandum C, Munich Diplomatic Conference, Sep. 1 to Oct. 6, 1973.

Minabe-Saegusa et. al., Genbank Sequence Database Accession No. AB011030, Jun. 23, 1998.

Minutes of EP2325199 Oral Proceedings dated Mar. 5, 2018.

Minutes of the oral proceedings before the opposition division for Opposition against European Patent No. 1721979, dated May 10, 2013.

Miyazono et. al., Divergence and convergence of TGF-(Beta)/BMP signaling. J. Cell. Physiol., 187:265-76 (2001).

Miyazono et. al., TGF-(beta) signaling by Smad proteins. Adv. Immunology, 75:115-57 (2000).

Morais et al., In vitro biomineralization by osteoblast-like cells I. Retardation of tissue mineralization by metal salts. Biomaterials, 19: 13-21 (1998).

Mori et al., A novel amino acid substitution a the receptor-binding site on the hemaglutinin of H3N2 influenza A viruses isolated from 6 cases with acute encephalopathy during 1997-1998 season in Tokyo. Arch. Virol., 144: 147-55 (1999).

(56) References Cited

OTHER PUBLICATIONS

Morrison et al., ATP is a potent stimulator of the activiation and formation of rodent osteoclasts. J. Physiol., 511.2: 495-500 (1998).

Mosekilde et al., Assessing bone quality—Animcal models in preclinincal osteoporosis research. Bone, 17 (4): 343S-52S (1995).

Moult, The current state of the art in protein structure predicion. Curr. Opin. Biotech., 7(4):422-7 (1996).

Mullins et. al., Perspectives series: Molecular medicine in genetically engineered animals; Transgenesis in the rat and larger mammals. J. Clin. Invest., 97(7):1557-60 (1996).

Muntoni et. al., A mutation in the dystrophin gene selectively affecting dystrophin expression in the heart. J. Clin. Invest., 96: 693-9 (1995).

Nagaraja et al., X chromosome map at 75-kb STS resolution, revealing extremes of recombination and GC content. Genome Res. 7: 210-22 (1997).

Nakase et. al., Transient and localized expression of bone morphogenetic protein 4 messenger RNA during fracture healing. J. Bone Miner. Res., 9(5):651-9 (1994).

Nelson, Positional cloning reaches maturity. Curr. Opin. Genet. Devel., 5:298-303 (1995).

Nickel et al., The crystal structure of the BMP-2: BMPR-1 A complex and the generation of BMP-2 antagonists. J. Bone Joint Surg., 83-A:S1-7-S1-14 (2001).

Nicolas et. al., An age-related decrease in the concentration of insulin-like growth factor binding protein-5 in human cortical bone. Calcit. Tissue Int., 57:206-12 (1995).

Niessen, Liquid Chromatography- Mass Spectrometry, 3rd Ed. (2006 ).

Nifuji et. al., Coordinated expression of noggin and bone morphogenetic proteins (BMPs) during early skeletogenesi and induction of noggin expression by BMP-7. J. Bone Miner. Res., 14(12):2057-66 (1999).

Nisonoff et. al., Separation of univalent fragments from the bivalent rabbit antidody molecule by reduction of disulfide bonds. Arch. Biochem. Biophys., 89:230-44 (1960).

Niu et al., Sclerostin inhibition leads to increased periosteal and endocortical bone formation as well as decreased cortical porosity in aged ovariectomized rats. J. Bone Min. Res., 22(Suppl. S1) S65 (2007).

Nordsletten et. al., The neuronal regulation of fracture healing. Acta Orthop Scand., 65(3): 299-304 (1994).

Notice of Opposition against European Patent No. 1133558, Opponent: Eli Lilly and Company, dated May 31, 2007.

Declaration of Professor Teresa Attwood, citation in Appeal, European Patent No. 1133558, dated Apr. 13, 2010.

Declaration of Tim Arnett, citation in Appeal, European Patent No. 1133558, dated Apr. 2, 2010.

Delmas et al., The use of biochemical markers of bone turnover in osteoporosis. Osteoporosis International., Suppl. 6:S2-17 (2000).

Diagram of the candidate interval, citation by Propriator in Opposition against European Patent No. 1721979 on Feb. 20, 2012.

Drake et al., Current Trends in Monoclonal Antibody Development and Manufacturing, Chapter 11, "Characterizing High Affinity Antigen/Antibody Complexes by Kinetic and Equilibrium Based Methods", pp. 179-192(2010).

Ducy et al., Genetic control of cell differentiation in the skeleton. Curr. Opin. Cell Biol., 10: 614-9 (1998).

Ducy et. al., 5-HT and bone biology. Curr. Opin. Pharmacol., 11: 34-8 (2011).

Durham et al., Alterations in insulin-like growth factor (IGF)-dependent IGF-binding protein-4 proteolysis in transformed osteoblastic cells. Endocrinology, 136(4):1374-80 (1995).

Ebara et al., Mechanism for the action of bone morphogenetic proteins and regulation of their activity. Spine, 27(165):S10-5 (2002).

Eli Lilly Statement of Grounds of Appeal, Opposition to European Patent Application No. 1133558 B1, dated Sep. 28, 2009.

Eli Lilly, Biacore experiment comparison results, Setup assay to measure BMP binding to captured SOST, referenced on paqe 41 of reference C193, dated Sep. 28, 2009.

Epstein et al., Endocrine function in sclersteosis. S. Afr. Med. J., 55:1105-10 (1979).

European Patent Office Communication, Opposition to European Patent No. 1133558, dated Nov. 4, 2008.

European Patent Office, "Opinion of the Enlarged Board of Appeal dated Dec. 1992 G 1/92", available from [http://documents.epo.org/projects/babylon/eponet.nsf/0/907016FA57B46FDOC12572C8006CD2E2/$File/g920001.odfl, cited Jun. 15, 2011.

Expert Opinion from Dr. Catalina Lopez-Correa, submitted in Opposition to European Patent No. 1133558, dated Mar. 6, 2009.

Expert opinion of Professor Dr.-Ing Ulrich Vollrath, citation in Appeal of European Patent No. 1133558, dated Apr. 12, 2005.

Extract from Sigma Aldrich catalogue, cited in Opposition against European Patent No. 1721979 by Opponent: Laudens, dated Jun. 15, 2011.

Eyre et al., Characterization of aromatase and 1713-hydroxysteroid dehydrogenase expression in rat osteoblastic cells. J. Bone Miner. Res., 13(6): 996-1004 (1998).

Foster et al., Establishment of interference in osteoblasts by an osteopetrosis-inducing Avian Leukosis virus. Virology, 205: 376-8 (1994).

Fouser et al., Feedback regulation of collagen gene expression: A Trojan horse approach. Proc. Natl. Acad. Sci. USA, 88: 10158-62 (1991).

Frost et. al., On the rat model of human osteopenias and osteoporoses. Bone and Mineral, 18:227-36 (1992).

Fujiwara et al., GenBank Sequence Database Accession No. 079813, Feb. 9, 1996.

Gardner et al., Bone mineral density in sclerosteosis; Affected individuals and gene carriers. J. Clin. Endocrinol. Metab., 90(12): 6392-5 (2005).

Gavarini et al., Opposite effects of PSD-95 and MPP3 PDZ proteins on serotonin 5- hydroxytryptamine2C receptor desensitization and membrane stability. Malec. Biol., 17: 4619-31 (2006).

Gazzerro et al., Bone morphogenetic proteins induce the expression of noggin which limits their activity in cultured rat osteoblasts. J. Clin. Invest., 102(12):2106-14 (1998).

Gazzerro et al., Potential drug targets within bone morphogenetic protein signaling pathways. Curr. Opin. Pharmacol., 7: 325-3 (2007).

Geissler et la., Male pseudohermaphroditism caused by mutations of testicular 1713-hydroxysteroid hehydrogenase 3. Nat. Genetics, 7: 34-9 (1994).

Gencic et. al., Conservative amino acid substitution in the myelin proteolipid protein of Jimpymsd mice. J. Neurosci., 10(1):117-24 (1990).

Geysen et. al., Cognitive features of continuous antigenic determinants. J. Malec. Recog., 1(1):32-41 (1988).

Gitelman et al., Vgr-1/BMP-6 induces osteoblastic differentiation of pluripotential mesenchymal cells. Cell Growth & Differentiation, 6:827-36 (1995).

Glasky et al., Stability of specific immunoglobulin secretion by EBV-transformed lymphoblastoid cells and human-murine heterohybridomas. Hybridoma, 8: 377-89 (1989).

Glorieux et al., BPS804 Anti-Sclerostin Antibody in Adults with Moderate Osteogenesis Imperfecta: Results of a Randomized Phase 2a Trial, J. Bone. Min Res. 32(7):1496-1504 (2017).

Gowen et al., Actions of recombinant human y-interferon and tumor necrosis factor a on the proliferation and osteoblastic characteristics of human trabecular bone cells in vitro. Arthritis Rheumatism, 31(12): 1500-7 (1988).

Graner et al., Splice variants of the Drosophila PS2 integrins differentially interact with RGD—containing fragments of the extracellular proteins tiggrin, Ten-m and D-laminin a2. J. Biol. Chem., 273(29): 18235-41 (1998).

Grappe et. al., Structural basis of BMP signalling inhibition by the cystine knot protein noggin. Nature, 420:636-42 (2002).

Green et al., Cytosolic pH regulation in osteoblasts. J. Gen. Physiol., 95: 121-45 (1990).

(56)        References Cited

OTHER PUBLICATIONS

Green et. al., Antigen-specific human monoclonal antibodies from mice engineered with human Ig heavy and light chain YACs. Nat. Genet., 7:13 (1994).
Greene et. al., Screening Recombinant DNA Libraries. Current Protocols in Molecular Biology, Ch. 6(1) (1990).
Gribskov et al., Profile analysis. Meth. Enzym., 183:146-59 (1990).
Gribskov et. al., Profile analysis: Detection of distantly related proteins. Proc. Nat. Acad. Sci. USA, 84(13):4355-8 (1987).
Groeneveld et al., "Bone Morphogenetic Proteins in Human Bone Regeneration," Eur. J. Endocrinol., 142:9-21 (2000).
Gronthos et. al., Integrin expression and function on human osteoblast-like cells. J. Bone Miner. Res., 12(8): 1189-97 (1997).
Guinness-Hey, Increased trabecular bone mass in rats treated with human synthetic parathyroid hormone. Metab. Bone Dis. Relat. Res., 5:177-81 (1984).
Harlow et al., "Antibodies: A Laboratory Manual," Cold Spring Harbor Laboratory, 141-157 (1988).
Harris, Processing of C-terminal lysine and arginine residues of proteins isolated from mammalian cell culture. J. Chromatoqr., 705:129-34 (1995).
Hart et al., Crystal structure of the human TI3R2 ectodomain-TGF-133 complex. Nat. Struc. Biol., 9(3):203-8 (2002).
Hay et. al., ATCC Cell Line and Hybridomas, American Type Culture Collection, 8th Ed., pp. 149, 258,428 (1994).
He et al., High-throughput dynamic light scattering method for measuring viscosity of concentrated protein solutions. Anal. Biochem., 399(1): 141-3 (2010).
Heinecke et al., Receptor oligomerization and beyond: A case study in bone morphogenetic proteins, BMC Biol., 7: 59 (2009).
Hill et. al., Multiple extracellular signals promote osteoblast survival and apoptosis. Endocrinology, 138(9):3849-58 (1997).
Hillier et al., Generation and analysis of 280,000 human expressed sequence tags. Genome Res., 6: 807-28 (1996).
Hillier et. al., EMBL Sequence Database Accession No. AA393939, May 19, 1997.
Hillier et. al., GenBank Sequence Database Accession No. AA393768, Apr. 24, 1997.
Hilliker et al., Truncation of the amino terminus of PTH alters its anabolic activity on bone in vivo. Bone, 19(5): 469-77 (1996).
Hirschhorn, Letter to the Editor: Dominance and Homozygosity in Man. Am. J. Med. Genetics, 18: 541 (1984).
Hock et al., Perspective: Osteoblast apoptosis and bone turnover. J. Bone Miner. Res., 16(6): 975-84 (2001).
Hoffman et. al., BMP Signaling Pathways in Cartilage and Bone Formation, Grit. Rev. Eukaryotic Gene Exp., 11(1-3):23-45 (2001).
Hoggard et al., Localization of leptin receptor mRNA splice variants in murine peripheral tissues by RT-PCR and in situ hybridization. Biochem. Biophys. Res. Commun., 232: 383-7 (1997).
Hollinger et al., Engineered antibody fragments and the rise of single domains. Nat. Biotech., 23(9):1126-36 (2005).
Holm et al., Protein folds and families: Sequence and structure alignments. Nucl. Acid Res., 27(1):244-7 (1999).
Holt et al., Domain antibodies: proteins for therapy, Trends Biotechnol. 21(11):484-90 (2003).
Hoogenboom et al., By-passing immunisation: Human antibodies from synthetic repertoires of germline VH gene segmens rearranged in vitro. J. Malec. Biol., 227:381-8 (1992).
Hoogewerf et al., Glycosaminoglycans mediate cell surface oligomerization of chemokines. Biochemistry, 36: 13570-8 (1997).
Horton et. al., Arg-Gly-Asp (RGD) peptides and the anti-vitronectin receptor antibody 23C6 inhibit dentine resorption and cell spreading by osteoclasts. Exp. Cell Res., 195: 368-75 (1991).
Hsu et. al., The Xenopus dorsalizing factor gremlin indentified a novel family of secreted proteins that antagonize BMP activities. Malec. Cell, 1:673-83 (1998).
Hufner et al., Evidence for an osteoblast-activating factor in a patient with peripheral T-cell lymphoma and osteosclerosis. Klin. Wochenscher., 67: 402-7 (1989).

Hugo et al., Functional aspects of co-variant surface charges in an antibody fragment, Protein Science, 11:2697-705 (2002).
Hulley et al., Inhibition of mitogen-activated protein kinase activity and proliferation of an early osteoblast cell line (MBA 15.4) by dexamethasone: Role of protein phosphatases. Endocrinol., 139(5): 2423-31 (1998).
Huse et al., Generation of a large combinatorial library of the immunoglobulin repertoire in phage lambda. Science, 246:1275-81 (1989).
Hwang et. al., Use of human germline genes in a CDR homoloy-based approach to antibody humanization. Methods, 36(1):35-42 (2005).
Ide et al., GenBank Sequence Database Accession No. BAA19765, Feb. 7, 1999.
Ide et. al., GenBank Sequence Datacase Accession No. 089675, Feb. 7, 1999.
Innis et. al., Evolutionary trace analysis of TGF-B and related growth factors: Implications for stie-directed mutagenesis. Protein Engineering, 13(12):839-47 (2000).
International Application No. PCT/US2019/024739, International Preliminary Report on Patentability, mailed Oct. 15, 2020.
International Application No. PCT/US2019/024739, International Search Report and Written Opinion, mailed Aug. 8, 2019.
Jakobovits et al., Production of antigen-specific human antibodies from mice engineered with human heavy and light chain YACsa. Ann. N.Y. Acad. Sci., 764:525-35 (1995).
Jee et al., Overview: Animal models of osteopenia and osteoporosis. J. Musculoskel. Neuron. Interact., 1:193-207 (2001).
Jilka et al., Increased bone formation by prevention of osteoblast apoptosis with parathyroid hormone. J. Clin. Invest. 104: 439-46 (1999).
Jilka et al., Osteoblast programmed cell death (apoptosis): Modulation by growth factors and cytokines. J. Bone Miner. Res., 13(5): 793-802 (1998).
Jones, Progress in protein structure predication. Curr. Opin. Struct. Biol., 7(3):377-387 (1997).
Kabat et al., Sequences of Proteins of Immunological Interest, U.S. Department of Health and Human Services, NIH, USA (1987) (Table of Contents).
Kalu, The ovariectomized rat model of postmenopausal bone loss. Bone and Mineral, 15:175-92 (1991).
Kang et al., Linkage of recognition and replication functions by assembling combinatorial antibody Fab libraries along phage surfaces. Proc. Natl. Acad. Sci. USA, 88:4363-6 (1991).
Katagiri et al., The non-osteogenic mouse pluripotent cell line, C3H1OT1/2, is induced to differentiate into osteoblastic cells by recombinant human bone morphogenetic protein-2. Biochem. Biophys. Res. Comm., 172(1):295-9 (1990).
Kawabata et. al., Signal transduction by bone morphogenetic proteins. Cytokine and Growth Factor Reviews, 9(1):49-61 (1998).
Keller et. al., Molecular recognition of BMP-2 and BMP receptor IA. Nat. Struct. Mol. Biol., 11(5):481-488 (2004).
Khalil, TGF-Beta: From latent to active. Microbes and Infection, 1(15):1255-63 (1999).
Khosla et. al., Concise review for primary-care physicians. Treatment pptions for osteoporosis. Mayo Clin. Proc., 70:978-82 (1995).
Kirsch et. al., BMP-2 antagonists emerge from alterations in the low-affinity binding epitope for receptor BMPR-II, EMBO J., 19(13): 3314-24 (2000).
Kohler et. al., Continuous cultures of fused cells secreting antibody of predefined specificity. Nature, 256:495 (1975).
Koli et. al., Latency, activation, and binding proteins of TGF-. Microscopy Res. Tech., 52:354-62 (2001).
Koreth et al., Microsatellites and PCR genomic analysis. J. Pathology, 178:239-48 (1996).
Kramer et. al., The gapped duplex DNA approach to oligonucleotide-directed mutation construction. Nuc. Acids Res., 12:9441 (1984).
Krause et. al., Distinct modes of inhibition by sclerostin on bone morphogenetic protein and Wnt signaling pathways. J. Biol. Chem., 285(53): 41614-26 (2010).
Kunkel et. al., Rapid and efficient site-specific mutagenesis without phenoypic selection. Meth. Enzymol., 154:367-82 (1987).

(56) References Cited

OTHER PUBLICATIONS

Kunkel, Rapid and efficient site-specific mutagenesis without phenotypic selection. Proc. Natl. Acad. Sci. USA, 82:488-92 (1985).

Kurahashi et al., Regions of genomic instability on 22q11 and 11q23 as the etiology for the recurrent constitutional t (11;22). Hum. Malec. Genet., 9: 1665-70 (2000).

Kusu et al., Sclerostin is a novel secreted osteoclast-dervied bone morphogenetic protein antagonist with unique liqand specificity. J. Biol. Chem., 278:24113-7 (2003).

Labat et. al., Retroviral expression in mononuclear blood cells isolated from a patient with osteopetrosis (Albers-Schonberg disease). J. Bone Miner. Res., 5(5): 425-35 (1989).

Labat, A new approach to the study of the origin of genetic disease: Retroviral etiology of osteopetrosis. Biomed. Pharmacother., 45: 23-7 (1991).

Takakura, Drug delivery systems in gene therapy. Nippon Rinsho, 56(3):691-5 (1998) (Abstract Only).

Takeda et al., GenBank Sequence Database Accession No. 038082, dated Dec. 27, 2006.

Takeda et al., GenBank Sequence Database Accession No. AAB33865, May 27, 1995.

Takeda et al., NCBI Sequence Database Accession No. NM_030849, Feb. 11, 2009.

Takeda et. al., GenBank Sequence Database Accession No. S75359, May 27, 1995.

Takeda, Expression of serine/threonine kinase receptors during ectopic bone formation induced by bone morphogenetic protein (BMP). Kokubyo Gakkai Zasshi, 61(4):512-26 (1994).

Tam et al., TGF-13 receptor expression on human keratinocytes: A 150 kDa GPI-anchored TGF-131 binding protein forms a heteromeric complex with type I and type II receptors. J. Cellular Biochem., 70:573-56 (1998).

Taylor et al., Human immunoglobulin transgenes undergo rearrangement, somatic mutation and class switching in mice that lack endogenous IgM. Int. Immun., 6:579 (1994).

The Merck Manual-Second Home Edition, Ch. 61:1-3 (2005).

Thompson et al., Affinity maturation of a high-affinity human monoclonal antibody against the third hypervariable loop of human immunodeficiency virus: Use of phage display to improve affinity and broaden strain reactivity. J. Mol. Biol. 256: 7-88 (1996).

Thornton et. al., Prediction of progress at last. Nature, 354:105-6 (1991).

Tjaderhane et al., A high sucrose diet decreases the mechanical strength of bones in growing rats. J. Nutr., 128: 1807-10 (1998).

Tsubaki et al., C-terminal modification of monoclonal antibody drugs: Amidated species as a general product-related substance, Int. J. Biol. Macromol., 52:139-47 (2013).

Tuncay et al., Oxygen tension regulates osteoblast function. Am. J. Orthod. Dentofac. Orthop., 105: 457-63 (1994).

UCB and Amgen announce positive phase 2 results of CDP7851/AMG785 in patients with post menopausal osteoporosis (PMO), dated Apr. 21, 2011—Citation in Opposition against European Patent No. 1721979.

Uitterlinden et. al., Relation of alleles of the collagen type la1 gene to bone density and the risk of osteoporotic fractures in postmenopausal women. New Engl. J. Med., 338: 1016-21 (1998).

Utting et al., Hypoxia stimulates osteoclast formation from human peripheral blood. Cell Biochem. Funct., 28:374-80 (2010).

Valero et. al., Quaternary structure of casein kinase 2. J. Biol. Chem., 27(14): 8345-52 (1995).

Van Bezooijen et al., "Wnt but Not BMP Signaling Is Involved in the Inhibitory Action of Sclerostin on BMP-Stimulated Bone Formation," J. Bone. Miner. Res. 22:19-28 (2007).

Van Bezooijen et al., SOST/sclerostin, an osteocyte-derived negative regulator of bone formation, Cytokine Growth Factor Rev., 16: 319-27 (2005).

Van Bezooijen et. al., Sclerostin is an osteocyte-expressed negative regulator of bone formation, but not a classical BMP antagonist. J. Exo. Med., 199: 805-14 (2004).

Van Hui et al., Van Buchem Disease (hyperostosis corticalis generalisata) maps to chromosome 17q12-q21. Am. J. Hum. Genet., 2:391-9 (1998).

Vanier et. al., Recent advances in elucidating Niemann-Pick C disease. Brain Pathol., 8: 163-74 (1998).

Verges et al., NCBI Sequence Database Accession No. NM_001203, Jul. 12, 2009.

Verges et al., NCBI Sequence Database Accession No. NP_001194, Jul. 12, 2009.

Veverka et. al., Characterization of the structural features and interactions of sclerostin. J. Biol. Chem., 284(16): 10890-900 (2009).

Viter et. al., Analysis of antigenic structure of potato virus M Ukrainian strains. Biopolimery I Kletka, Naukova Dumka, Kiev K, UK, 16: 312-9 (2000).

Von Bubnoff et al., "Intracellular BMP Signaling Regulation in Vertebrates: Pathway or Network?" Dev. Biol., 239:1-14 (2001).

Wall, "Transgenic Livestock: Progress and Prospects for the Future," Theriogenology, 45:57-68 (1996).

Wang et al., IFP 35 forms complexes with B-ATF, a member of the AP1 family of transcription factors. Biochem. Biophys. Res. Commun., 229: 316-22 (1996).

Wang, Bone morphogenetic proteins (BMPs): Therapeutic potential in healing bony defects. TIBTECH, 11:379-83 (1993).

Warmington et al., Oasis Online Abstract Submission and Invitation System—Program Planner, "Sclerostin Monoclonal Antibody Treatment of Osteoporotic Rats Completely Reverses One Year of Ovariectomy-Induced Systemic Bone Loss" downloaded Nov. 23, 2015.

Warmington et al., Presentation 1217 at American Society for bone and Mineral Research annual meeting Seattle (Oct. 2004).

Warmington et. al., Sclerostin antagonism in adult rodents, via monoclonal antibody mediated blockade, increases bone mineral density and implicates sclerostia as a key regulator of bone mass during adulthood. J. Bone Min. Res., 19:S56-7 (2004).

Warmington et. al., Sclerostin monoclonal antibody treatment of osteoporotic rats completely reverses one year of overiectomy-induced systemic bone loss. J. Bone Min. Res., 20:S22 (2005).

Winkler et al., Noggin and sclerostin bone morphogenetic protein antagonists form a mutually inhibitory complex. J. Biol. Chem., 279(35): 36296-8 (2004).

Winkler et al., Osteocyte control of bone formation via sclerostin, a novel BMP antagonist. EMBO J. 22: 6267-76 (2003).

Winkler et al., Sclerostin inhibition of Wnt-3a-induced C3H10T1/2 cell differentiation is indirect and mediated by bone morphogenetic proteins. J. Biol. Chem. 280: 2498-502 (2005).

Winter et. al., Making antibodies by phase display technology. Annu. Rev. Immunol., 12:433-55 (1994).

Wolff et al., Monoclonal antibody homodimers: enhanced antitumor activity in nude mice. Cancer Res. 53: 2560-5 (1993).

Wollenberger et al. (Eds.), Analytische Biochemie, Chapter 3, pp. 47-49 (2003).

Written Decision to Revoke EP 2556841, dated Jul. 19, 2018.

Written submission—Observation by a Third Party According to Art. 115 EPC, Opposition to European Patent No. 1133558, dated Nov. 25, 2008.

Written submission in response to summons to oral proceedings in Opposition against European Patent No. 1721979, Oooonent: Eli Lilly Company, dated Feb. 25, 2013.

Written submission in response to summons to oral proceedings in Opposition against European Patent No. 1721979, Opponent: Norvartis AG, dated Feb. 25, 2013.

Written submission of Eli Lilly & Company to European Patent Office, Opposition to European Patent No. 1133558, dated May 29, 2007.

Written Submission of Eli Lilly & Company, Opposition to European Patent No. 1133558, dated Mar. 9, 2009.

Written Submission of Opponent in response to summons to oral proceedings in Opposition against European Patent No. 2556841, dated Feb. 16, 2018.

Written submission of UCB S.A., Proprietor's Preliminary Response to the Opponent's submission of Mar. 9, 2009, Opposition to European Patent No. 1133558, dated Mar. 20, 2009.

(56) References Cited

OTHER PUBLICATIONS

Written submission of UCB S.A., Proprietor's Response to Opposition against European Patent No. 1133558, dated Mar. 14, 2008.

Written Submission, Proprietor's reply to the Notice of Opposition against European Patent No. 2556841, dated Jul. 25, 2017.

Yanagita et al., USAG-1: A bone morphogenetic protein antagonist abundantly expressed in the kidney. Biochem. Biophys. Res. Comm. 316: 490-550 (2004).

Yang et al., CDR walking mutagenesis for the affinity maturation of a potent human anti-HIV-1 antibody into the picomolar range, J. Mol. Biol. 254:392-403 (1995).

Yates et al., Inhibition of bone resorption by inorganic phosphate in mediated by both reduced osteoclast formation and decreased activity of mature osteoclasts. J. Bone Miner. Res., 6(5): 476-8 (1990).

Yoshida et al., Osteoinduction capability of recombinant human bone morphogenetic protein-2 in intramuscular and subcutaneous sites: An experimental study. J. Cranio-Maxillofac. Surg., 26: 112-5 (1998).

Zambaux et. al., Influence of experimental parameters on the characteristics of poly(lactic acid) nanoparticles prepared by a double emulsion method. J. Controlled Rel., 50(1-3):31-40 (1998).

Zhang et. al., Humanization of an anti-human TNF-13 antibody by variable region resurfacing with the aid of molecular modeling. Malec. Immunol., 42(12): 1445-51 (2005).

Zimmerman et al., The spemann organizer signal noggin binds and inactives bone morphogenetic protein 4. Cell, 86(4):599-606 (1996).

Zlotogora et. al., Dominance and homozygosity. Am. J. Med. Genet., 68: 412-6 (1997).

Zur Muhlen et al., Solid lipid nanoparticles (SLN) for controlled drug delivery—Drug release and release mechanism. Eur. J. Pharm. Biopharm., 45(2):149-55 (1998).

Robb et al., Atmospheric Pressure Photoionization: An Ionization Method for Liquid Chromatogreapy—Mass Spectrometry, Anal. Chem. 72:3653-59 (40000).

Roberts et al., Essential functional interactions of SAFA, a *Saccharomyces cerevisiae* complex of Spt, Ada, and Gcn5 proteins, with the Snf/Swi and Srb/Mediator complexes. Genetics, 147: 451-65 (1997).

Robinson et al., The sclerostin antibody project. Hum. Antibodies, 16: 36 (2007).

Rosenzweig et al., "Cloning and characterization of a human type 11 receptor for bone morphogenetic proteins," Proc. Natl. Acad. Sci, USA, 92:7632-7636 (1995).

Rosenzweig et al., GenBank Sequence Database Accession No. CAA88759, Oct. 7, 2008.

Rosenzweig et al., GenBank Sequence Database Accession No. Z48923, Oct. 7, 2008.

Rudikoff et al., Single amino acid substitution altering antigen-binding specificity, Proc. Natl. Acad. Sci. USA. 79:1979-83 (1982).

Ruppert et. al., Human bone morphogenetic protein 2 contains a heparin-binding site which modifies its biological activity. Eur. J. Biochem., 237: 295-302 (1996).

Sada et al., Adsorption equilibirum in immuno-affinity chromatography with polyclonal and monoclonal antibodies. Biotechnol. Bioengin., 28 (1986). Abstract.

Sali et al., Comparative protein modeling by satisfaction of spatial restraints. J. Mol. Biol., 234(3):779-815 (1993).

Sambrook et al., "Synthetic Oligonucleotide Probes," Molecular Cloning—A Laboratory Manual, Ch. 11:11.1-11.19 and 11.58-11.61 (1989).

Sanger et. al., DNA sequencing with chain-terminating inhibitors. Proc. Natl. Acad. Sci. USA, 74:5463-7 (1997).

Sastry et. al., Cloning of the immunological repertoire in *Escherichia coli* for generation of monoclonal catalytic antibodies: Construction of a heavy chain variable region-specific cDNA library. Proc. Natl. Acad. Sci. USA, 86:5728-32 (1989).

Scatchard et. al., The attractions of proteins for small molecules and ions. Ann. N.Y. Acad. Sci., 51:660-72 (1949).

Scheufler et. al., Crystal structure of human bone morphogenetic protein-2 at 2.7 A resolution. J. Mo/. Biol., 287(1):101-15 (1999).

Schlebusch et al., Production of a single-chain fragment of the murine anti-idiotypic antibody ACA125 as phage-displayed and soluble antibody by recombinant phage antibody technique. Hybridoma, 16:47-52 (1997).

Schlunegger et al., Refined crystal structure of human transforming growth factor 132 at 1.95 A ResolutionJ. Mol. Biol., 231(2):445-458 (1993).

Schmidt et al., Retrovirus-induced osteopetrosis in mice: Effects of viral infection on osteogenic differentiation in skeletoblast cell cultures. Am. J. Pathol., 129(3): 503-10 (1987).

Schmitt et al., Bone morphogenetic proteins: An update on basic biology and clinical relevance. J. Orth. Res., 17:269-78 (1999).

Schwappacher et. al., NCBI Sequence Database Accession No. NM_001204, Aug. 16, 2009.

Scully et. al., BRCA1 is a component of the RNA polymerase II holoenzyme. Proc. Natl. Acad. Sci. USA, 94: 5605-10 (1997).

Second declaration of Martyn Robinson, citation in Appeal, European Patent No. 1133558, dated Apr. 15, 2010.

Serra et. al., Expression of a truncated, kinase-defective TGF-13 type II receptor in mouse skeletal tissue promotes terminal chondrocyte differentiation and osteoarthritis. J. Cell. Biol., 139(2):541-52 (1997).

Sigmund, Viewpoint: Are studies in genetically altered mice out of control? Arterioscler. Thromb. Vase. Biol., 20:1425-9 (2000).

Silverman et al., Sclerostin, J. Osteoporosis, 2010: 1-3 (2010).

Sippl et al., Threading thrills and threats. Structure, 4(1):15-19 (1996).

Siris, Clinical Review: Paget's disease of bone. J. Bone Miner. Res., 13(7): 1061-5 (1998).

Sivakumar et al., New insights into extracellular matrix assembly and reorganization from dynamic imaging of extracellular matrix proteins in living osteoblasts. J. Cell. Sci., 119(7):1350-60 (2006).

Skiple Skjerpen et al., Binding of FGF-1 variants to protein kinase CK2 correlates with mitogenicity. EMBO J. 21(15):4058-69 (2002).

Slater et al., Involvement of platelets in stimulating osteogenic activity. J. Orthopaedic Res., 13: 655-63 (1995).

Smith et al., Glucocorticoids inhibit development stage-specific osteoblast cell cycle. J. Biol. Chem., 275:19992-20001 (2000).

Smith, TGF (beta) inhibitors, new and unexpected requirements in vertebrate development. TIG, 15(1):3-5 (1999).

Sohocki et. al., A range of clinical phenotypes associated with mutations in CRX, a photoreceptor transcription-factor gene. Am. J. Hum. Genet., 63: 1307-15 (1998).

Spranger, International classification of osteochondrodysplasias, Eur. J. Pediatr., 151: 407-15 (1992).

Staehling-Hampton et al., A 52-kb deletion in the SOST-MEOX1 intergenic region on 17q12-q21 is associated with van Buchem disease in the Dutch population. Am. J. Med. Gen. 110: 144-52 (2002).

Stanley et al., DAN is a secreted glycopeotein related to Xenopus cerberus. Mech. Dev., 77: 173-84 (1998).

Statement of Grounds of Appeal to Decision of Opposition against European Patent No. 1133558, dated Sep. 28, 2009.

Stenmark et al., Distinct structural elements of rab5 define its functional specificity. EMBO J., 13(3): 575-83 (1994).

Strachan et. al. (Eds.), Diagram from text book entitled, Human Molecular Genetics, 2nd Edition (1999).

Strachan et. al. (Eds.), Human Molecular Genetics, 1st Edition, p. 420 (1996).

Strachan et. al., (Eds.), Human Molecular Genetics, 2nd Edition, Figure 15.4 (1999).

Submission in response to oral proceedings in Opposition against European Patent No. 1721979, Opponent: Eli Lilly, dated Apr. 24, 2013.

Sudo et al., In vitro differentiation and calcification in a new clonal osteogenic cell line derived from newborn mouse calvaria. J. Cell Biol., 96:191-8 (1983).

Summons to attend oral proceedings for Opposition against European Patent No. 1133558, dated Nov. 4, 2008.

Summons to attend oral proceedings in Opposition against European Patent No. 1721979, dated Nov. 12, 2012.

(56)        References Cited

OTHER PUBLICATIONS

Summons to attend oral proceedings regarding opposition against European Patent No. 2556841, dated Aug. 29, 2017.

Sutherland et al., Sclerostin romotes the apoptosis of human osteoblastic cells: A novel regulation of bone formation. Bone, 35:828-35 (2004).

Suzawa et al., Extracellular matrix-associated bone morphogenetic proteins are essential for differentiation of murine osteoblastic cells in vitro. Endocrinology, 140:2125-33 (1999).

Sverdlov et al., Perpetually mobile footprints of ancient infections in human genome. FEBS Lett., 428: 1-6 (1998).

Sylatron label, cited in Opposition against European Patent No. 1721979 by Opponent: Novartis AG, dated Jun. 15, 2011.

SEQUENCE LISTING

```
Sequence total quantity: 16
SEQ ID NO: 1              moltype = AA   length = 190
FEATURE                   Location/Qualifiers
REGION                    1..190
                          note = MISC_FEATURE - Human Sclerostin
source                    1..190
                          mol_type = protein
                          organism = Homo sapiens
```

-continued

```
SEQUENCE: 1
QGWQAFKNDA TEIIPELGEY PEPPPELENN KTMNRAENGG RPPHHPFETK DVSEYSCREL    60
HFTRYVTDGP CRSAKPVTEL VCSGQCGPAR LLPNAIGRGK WWRPSGPDFR CIPDRYRAQR   120
VQLLCPGGEA PRARKVRLVA SCKCKRLTRF HNQSELKDFG TEAARPQKGR KPRPRARSAK   180
ANQAELENAY                                                         190

SEQ ID NO: 2              moltype = AA  length = 5
FEATURE                   Location/Qualifiers
REGION                    1..5
                          note = MISC_FEATURE - romo HCDR1
source                    1..5
                          mol_type = protein
                          organism = Mus musculus
SEQUENCE: 2
DYNMH                                                               5

SEQ ID NO: 3              moltype = AA  length = 17
FEATURE                   Location/Qualifiers
REGION                    1..17
                          note = MISC_FEATURE - romo HCDR2
source                    1..17
                          mol_type = protein
                          organism = Mus musculus
SEQUENCE: 3
EINPNSGGAG YNQKFKG                                                  17

SEQ ID NO: 4              moltype = AA  length = 14
FEATURE                   Location/Qualifiers
REGION                    1..14
                          note = MISC_FEATURE - romo HCDR3
source                    1..14
                          mol_type = protein
                          organism = Mus musculus
SEQUENCE: 4
LGYDDIYDDW YFDV                                                     14

SEQ ID NO: 5              moltype = AA  length = 11
FEATURE                   Location/Qualifiers
REGION                    1..11
                          note = MISC_FEATURE - romoLCDR1
source                    1..11
                          mol_type = protein
                          organism = Mus musculus
SEQUENCE: 5
RASQDISNYL N                                                        11

SEQ ID NO: 6              moltype = AA  length = 7
FEATURE                   Location/Qualifiers
REGION                    1..7
                          note = MISC_FEATURE - romo LCDR2
source                    1..7
                          mol_type = protein
                          organism = Mus musculus
SEQUENCE: 6
YTSRLLS                                                             7

SEQ ID NO: 7              moltype = AA  length = 9
FEATURE                   Location/Qualifiers
REGION                    1..9
                          note = MISC_FEATURE - romo LCD3
source                    1..9
                          mol_type = protein
                          organism = Mus musculus
SEQUENCE: 7
QQGDTLPYT                                                           9

SEQ ID NO: 8              moltype = AA  length = 4
FEATURE                   Location/Qualifiers
REGION                    1..4
                          note = MISC_FEATURE - C-Terminal variant sequence
source                    1..4
                          mol_type = protein
                          organism = Homo sapiens
SEQUENCE: 8
PARG                                                                4

SEQ ID NO: 9              moltype = AA  length = 107
FEATURE                   Location/Qualifiers
source                    1..107
```

```
                         mol_type = protein
                         organism = Mus musculus
SEQUENCE: 9
DIQMTQSPSS LSASVGDRVT ITCRASQDIS NYLNWYQQKP GKAPKLLIYY TSRLLSGVPS    60
RFSGSGSGTD FTLTISSLQP EDFATYYCQQ GDTLPYTFGG GTKVEIK              107

SEQ ID NO: 10            moltype = AA   length = 123
FEATURE                  Location/Qualifiers
source                   1..123
                         mol_type = protein
                         organism = Mus musculus
SEQUENCE: 10
EVQLVQSGAE VKKPGASVKV SCKASGYTFT DYNMHWVRQA PGQGLEWMGE INPNSGGAGY    60
NQKFKGRVTM TTDTSTSTAY MELRSLRSDD TAVYYCARLG YDDIYDDWYF DVWGQGTTVT   120
VSS                                                               123

SEQ ID NO: 11            moltype = AA   length = 5
FEATURE                  Location/Qualifiers
REGION                   1..5
                         note = MISC_FEATURE - C-terminal variant sequence
source                   1..5
                         mol_type = protein
                         organism = Homo sapiens
SEQUENCE: 11
PARGK                                                               5

SEQ ID NO: 12            moltype = AA   length = 236
FEATURE                  Location/Qualifiers
REGION                   1..236
                         note = Humanized antibody sequence
REGION                   1..236
                         note = MISC_FEATURE - romo light chain
source                   1..236
                         mol_type = protein
                         organism = synthetic construct
SEQUENCE: 12
MDMRVPAQLL GLLLLWLRGA RCDIQMTQSP SSLSASVGDR VTITCRASQD ISNYLNWYQQ    60
KPGKAPKLLI YYTSRLLSGV PSRFSGSGSG TDFTLTISSL QPEDFATYYC QQGDTLPYTF   120
GGGTKVEIKR TVAAPSVFIF PPSDEQLKSG TASVVCLLNN FYPREAKVQW KVDNALQSGN   180
SQESVTEQDS KDSTYSLSST LTLSKADYEK HKVYACEVTH QGLSSPVTKS FNRGEC       236

SEQ ID NO: 13            moltype = AA   length = 469
FEATURE                  Location/Qualifiers
REGION                   1..469
                         note = Humanized antibody sequence
REGION                   1..469
                         note = MISC_FEATURE - romo heavy chain variant without
                          lysine
source                   1..469
                         mol_type = protein
                         organism = synthetic construct
SEQUENCE: 13
MDWTWRILFL VAAATGAHSE VQLVQSGAEV KKPGASVKVS CKASGYTFTD YNMHWVRQAP    60
GQGLEWMGEI NPNSGGAGYN QKFKGRVTMT TDTSTSTAYM ELRSLRSDDT AVYYCARLGY   120
DDIYDDWYFD VWGQGTTVTV SSASTKGPSV FPLAPCSRST SESTAALGCL VKDYFPEPVT   180
VSWNSGALTS GVHTFPAVLQ SSGLYSLSSV VTVPSSNFGT QTYTCNVDHK PSNTKVDKTV   240
ERKCCVECPP CPAPPVAGPS VFLFPPKPKD TLMISRTPEV TCVVVDVSHE DPEVQFNWYV   300
DGVEVHNAKT KPREEQFNST FRVVSVLTVV HQDWLNGKEY KCKVSNKGLP APIEKTISKT   360
KGQPREPQVY TLPPSREEMT KNQVSLTCLV KGFYPSDIAV EWESNGQPEN NYKTTPPMLD   420
SDGSFFLYSK LTVDKSRWQQ GNVFSCSVMH EALHNHYTQK SLSLSPARG              469

SEQ ID NO: 14            moltype = AA   length = 470
FEATURE                  Location/Qualifiers
REGION                   1..470
                         note = Humanizedantibody sequence
REGION                   1..470
                         note = MISC_FEATURE - romo heavy chain variant with lysine
source                   1..470
                         mol_type = protein
                         organism = synthetic construct
SEQUENCE: 14
MDWTWRILFL VAAATGAHSE VQLVQSGAEV KKPGASVKVS CKASGYTFTD YNMHWVRQAP    60
GQGLEWMGEI NPNSGGAGYN QKFKGRVTMT TDTSTSTAYM ELRSLRSDDT AVYYCARLGY   120
DDIYDDWYFD VWGQGTTVTV SSASTKGPSV FPLAPCSRST SESTAALGCL VKDYFPEPVT   180
VSWNSGALTS GVHTFPAVLQ SSGLYSLSSV VTVPSSNFGT QTYTCNVDHK PSNTKVDKTV   240
ERKCCVECPP CPAPPVAGPS VFLFPPKPKD TLMISRTPEV TCVVVDVSHE DPEVQFNWYV   300
DGVEVHNAKT KPREEQFNST FRVVSVLTVV HQDWLNGKEY KCKVSNKGLP APIEKTISKT   360
KGQPREPQVY TLPPSREEMT KNQVSLTCLV KGFYPSDIAV EWESNGQPEN NYKTTPPMLD   420
SDGSFFLYSK LTVDKSRWQQ GNVFSCSVMH EALHNHYTQK SLSLSPARGK             470
```

-continued

```
SEQ ID NO: 15          moltype = AA   length = 26
FEATURE                Location/Qualifiers
REGION                 1..26
                       note = MISC_FEATURE - amino acids 86-111 of SEQ ID NO: 1
source                 1..26
                       mol_type = protein
                       organism = Homo sapiens
SEQUENCE: 15
CGPARLLPNA IGRGKWWRPS GPDFRC                                      26

SEQ ID NO: 16          moltype = AA   length = 468
FEATURE                Location/Qualifiers
REGION                 1..468
                       note = Humanized Antibody sequence
REGION                 1..468
                       note = MISC_FEATURE - romo heavy chain wild type
source                 1..468
                       mol_type = protein
                       organism = synthetic construct
SEQUENCE: 16
MDWTWRILFL VAAATGAHSE VQLVQSGAEV KKPGASVKVS CKASGYTFTD YNMHWVRQAP  60
GQGLEWMGEI NPNSGGAGYN QKFKGRVTMT TDTSTSTAYM ELRSLRSDDT AVYYCARLGY  120
DDIYDDWYFD VWGQGTTVTV SSASTKGPSV FPLAPCSRST SESTAALGCL VKDYFPEPVT  180
VSWNSGALTS GVHTFPAVLQ SSGLYSLSSV VTVPSSNFGT QTYTCNVDHK PSNTKVDKTV  240
ERKCCVECPP CPAPPVAGPS VFLFPPKPKD TLMISRTPEV TCVVVDVSHE DPEVQFNWYV  300
DGVEVHNAKT KPREEQFNST FRVVSVLTVV HQDWLNGKEY KCKVSNKGLP APIEKTISKT  360
KGQPREPQVY TLPPSREEMT KNQVSLTCLV KGFYPSDIAV EWESNGQPEN NYKTTPPMLD  420
SDGSFFLYSK LTVDKSRWQQ GNVFSCSVMH EALHNHYTQK SLSLSPGK             468
```

C-TERMINAL ANTI-SCLEROSTIN ANTIBODY VARIANTS

CROSS-REFERENCE TO RELATED APPLICATIONS

The present application is a continuation of U.S. Application No. 17,934,585, filed Sep. 23, 2022 (now U.S. Pat. No. 11,585,983), which is a continuation application of U.S. application Ser. No. 16/971,590, filed Aug. 20, 2020, (now U.S. Pat. No. 11,466,079) which claims the benefit of priority to U.S. Provisional Application No. 62/650,762, filed Mar. 30, 2018, and U.S. Provisional Application No. 62/812,741, filed Mar. 1, 2019, the disclosures of which are incorporated herein by reference in their entireties.

TECHNICAL FIELD OF THE INVENTION

The invention generally relates to anti-sclerostin antibodies having at least one C-terminal modification and compositions comprising such antibodies.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: file name; "52080B_SeqListing.XML," 23,816 bytes, created on Nov. 29, 2023.

INCORPORATION BY REFERENCE

The following applications are hereby incorporated by reference in their entirety: International Patent Publication No. PCT/US2012/049331, filed Aug. 2, 2012, which claims priority to U.S. Provisional Patent Application No. 61/515, 191, filed Aug. 4, 2011; U.S. patent application Ser. No. 11/410,540, filed Apr. 25, 2006, which claims priority to U.S. Provisional Patent Application No. 60/792,645, filed Apr. 17, 2006, U.S. Provisional Patent Application No. 60/782,244, filed Mar. 13, 2006, U.S. Provisional Patent Application No. 60/776,847, filed Feb. 24, 2006, and U.S. Provisional Patent Application No. 60/677,583, filed May 3, 2005; and U.S. patent application Ser. No. 11/411,003 (issued as U.S. Pat. No. 7,592,429), filed Apr. 25, 2006, which claims priority to U.S. Provisional Patent Application No. 60/792,645, filed Apr. 17, 2006, U.S. Provisional Patent Application No. 60/782,244, filed Mar. 13, 2006, U.S. Provisional Patent Application No. 60/776,847, filed Feb. 24, 2006, and U.S. Provisional Patent Application No. 60/677,583, filed May 3, 2005. The following applications also are hereby incorporated by reference: U.S. patent application Ser. No. 12/212,327, filed Sep. 17, 2008, which claims priority to U.S. Provisional Patent Application No. 60/973,024, filed Sep. 17, 2007; and U.S. patent application Ser. No. 12/811,171, filed Jun. 29, 2010, which is a U.S. National Phase Application pursuant to 35 U.S.C. § 371 of International Patent Application No. PCT/US08/86864, filed on Dec. 15, 2008, which claims priority to U.S. Provisional Patent Application No. 61/013,917, filed Dec. 14, 2007.

BACKGROUND

Loss of bone mineral content can be caused by a wide variety of conditions and may result in significant medical problems. For example, osteoporosis is a debilitating disease in humans and is characterized by marked decreases in skeletal bone mass and mineral density, structural deterioration of bone, including degradation of bone microarchitecture and corresponding increases in bone fragility (i.e., decreases in bone strength), and susceptibility to fracture in afflicted individuals. Although osteoporosis has been regarded as an increase in the risk of fracture due to decreased bone mass, few of the presently available treatments for skeletal disorders can increase the bone density of adults, and most of the presently available treatments work primarily by inhibiting further bone resorption rather than stimulating new bone formation. Estrogen is now being prescribed to retard bone loss. However, some controversy exists over whether patients gain any long-term benefit and whether estrogen has any effect on patients over 75 years old. Moreover, use of estrogen is believed to increase the risk of breast and endometrial cancer. Calcitonin, osteocalcin with vitamin K, or high doses of dietary calcium, with or without vitamin D, have also been suggested for postmenopausal women. High doses of calcium, however, often have undesired gastrointestinal side effects, and serum and urinary calcium levels must be continuously monitored (e.g., Khosla and Riggs, Mayo Clin. Proc. 70:978982, 1995). Other current therapeutic approaches to osteoporosis include bisphosphonates (e.g., Fosamax™, Actonel™, Bonviva™, Zometa™, olpadronate, neridronate, skelid, bonefos), parathyroid hormone, calcilytics, calcimimetics (e.g., cinacalcet), statins, anabolic steroids, lanthanum and strontium salts, and sodium fluoride. Such therapeutics, however, are often associated with undesirable side effects (see Khosla and Riggs, supra).

Sclerostin, the product of the SOST gene, is absent in sclerosteosis, a skeletal disease characterized by bone overgrowth and strong dense bones (Brunkow et al., Am. J. Hum. Genet., 68:577-589, 2001; Balemans et al., Hum. Mol. Genet., 10:537-543, 2001). The amino acid sequence of human sclerostin is reported by Brunkow et al. ibid and is disclosed herein as SEQ ID NO:1. Sclerostin is valuable target for mediating increases in bone density.

SUMMARY

In one aspect, described herein is an antibody that specifically binds to sclerostin of SEQ ID NO: 1 and comprises a set of six CDRs set forth in SEQ ID NOs: 2-7, wherein the antibody comprises a heavy chain comprising the amino acid sequence Pro-Ala-Arg-Gly (SEQ ID NO: 8) at the C-terminus of the heavy chain. In some embodiments, the antibody comprises a light chain variable region comprising an amino acid sequence set forth in SEQ ID NO: 9 and a heavy chain variable region comprising an amino acid sequence set forth in SEQ ID NO: 10. In some embodiments, the antibody comprises the amino acid sequence Pro-Ala-Arg-Gly-Lys (SEQ ID NO: 11) at the C-terminus of the heavy chain. In some embodiments, the antibody comprises a first heavy chain comprising the amino acid sequence Pro-Ala-Arg-Gly (SEQ ID NO: 8) at the C-terminus of the first heavy chain and a second heavy chain comprising a wild-type heavy chain amino acid sequence (i.e., lacking the C-terminal Pro-Ala-Arg-Gly). In some embodiments, the antibody comprises the light chain amino acid sequence set forth in SEQ ID NO: 12 and the heavy chain amino acid sequence set forth in SEQ ID NO: 13. In some embodiments, the antibody comprises the amino acid sequence Pro-Ala-Arg-Gly-Lys (SEQ ID NO: 11) at the C-terminus of the heavy chain. In some embodiments, the antibody comprises the light chain amino acid sequence set forth in SEQ ID NO: 12 and the heavy chain amino acid sequence set forth in SEQ ID NO: 14.

In some embodiments, the C-terminus of one of the heavy chains of the antibody is amidated (i.e., the antibody is singly amidated). In some embodiments, the C-terminus of both heavy chains of the antibody is amidated (i.e., the antibody is double amidated).

Pharmaceutical compositions comprising a population of the antibodies described herein and a pharmaceutically acceptable carrier are also provided by the disclosure. In some embodiments, the pharmaceutical composition comprises a mixture of antibodies that specifically bind to sclerostin of SEQ ID NO: 1, wherein the mixture of antibodies comprises a population of antibodies comprising a heavy chain having the amino acid sequence Pro-Ala-Arg-Gly (SEQ ID NO: 8) at the C-terminus of the heavy chain and a pharmaceutically acceptable carrier. In some embodiments, about 3-5% of the antibodies in the composition are a population of the antibodies comprising a heavy chain having the amino acid sequence Pro-Ala-Arg-Gly (SEQ ID NO: 8) at the C-terminus of the heavy chain. In some aspects, less than 70% of the population of antibodies are amidated on one or both heavy chains. In some aspects, all or part of the population of antibodies comprise a single heavy chain comprising a C-terminal Pro-Ala-Arg-Gly (SEQ ID NO: 8) sequence, which is optionally amidated. In some aspects, all or part of the population of antibodies comprise a C-terminal Pro-Ala-Arg-Gly (SEQ ID NO: 8) sequence in both heavy chains, and both heavy chains are optionally amidated. Optionally, less than about 35% of the population of antibodies is singly amidated and/or less than about 35% of the population of antibodies are amidated on both heavy chains and/or less than about 35% of the population of antibodies comprise heavy chains that are not amidated. In this regard, in various aspects, about 33% of the population of antibodies are not amidated, about 33% of the population of antibodies comprise one amidated heavy chain, and about 33% of the population of antibodies comprise two amidated heavy chains.

In some embodiments, the composition further comprises a calcium salt, an acetate buffer, a polyol and a surfactant. In some embodiments, the acetate salt comprises calcium acetate, the acetate buffer comprises sodium acetate, the polyol comprises sucrose and the surfactant comprises polysorbate 20. In some embodiments, the composition comprises 55 mM acetate, 13 mm calcium, 6.0% (w/v) sucrose, and 0.006% (w/v) polysorbate 20, pH 5.2.

Also provided by the disclosure is a method of increasing bone mineral density in a subject in need thereof comprising administering the composition described herein to the subject in an amount effective to increase bone mineral density in the subject.

BRIEF DESCRIPTION OF THE FIGURES

FIG. 3 is a graph showing the percent recovery from the Scissor model of a subcutaneous injection shown as a function of time. Wild type romosozumab (circles) and PARG (SEQ ID NO: 8) c-terminal variant romosozumab diffuse at different rates for the simulated injection site.

Figure 4:
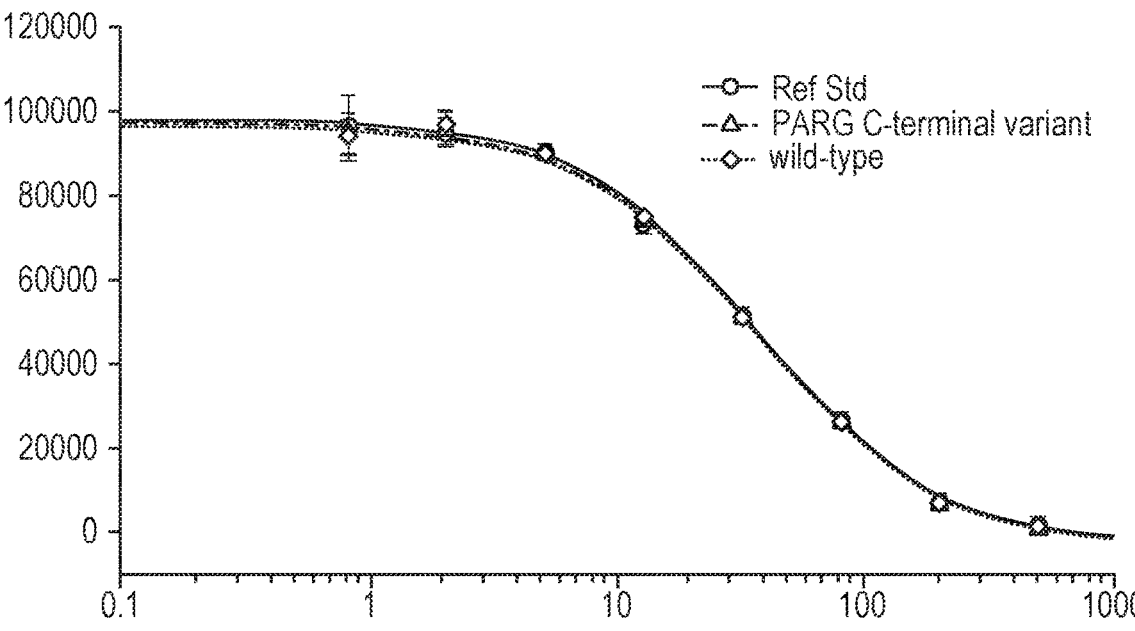

FIG. 4 is a graph showing that both wild type romosozumab and PARG (SEQ ID NO: 8) C-terminal variant romosozumab bound FcRn similarly and that FcRn binding was not affected by the PARG (SEQ ID NO: 8) mutation.

Figure 5:
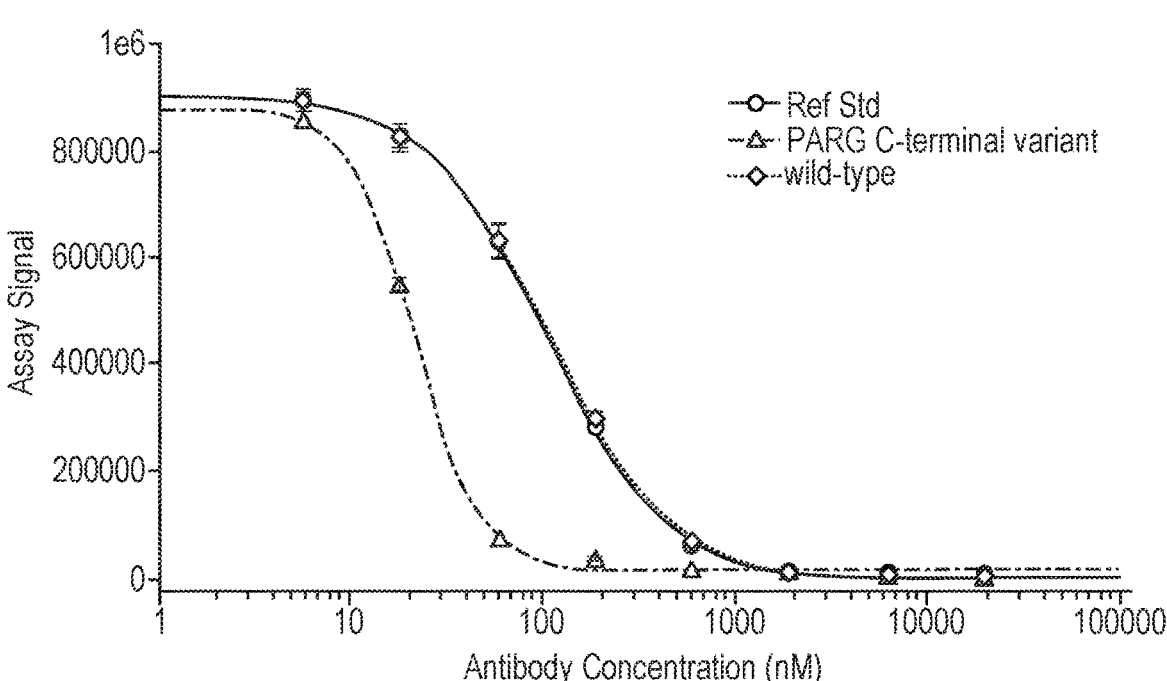

FIG. 5 is a graph showing that the relative binding of PARG (SEQ ID NO: 8) C-terminal variant romosozumab to FcγRIIa (131H) was much higher than wild-type romosozumab.

DETAILED DESCRIPTION

The disclosure provides an antibody that specifically binds to sclerostin, wherein the antibody comprises a heavy chain comprising a sequence of amino acids comprising Pro-Ala-Arg-Gly (SEQ ID NO: 8) at the C-terminus of the heavy chain. In some embodiments, the antibody comprises a first heavy comprising a sequence of amino acids comprising Pro-Ala-Arg-Gly (SEQ ID NO: 8) at the C-terminus of the heavy chain and a second heavy chain comprising a wild-type heavy chain amino acid sequence. In some embodiments, the antibody comprises a sequence of amino acids comprising Pro-Ala-Arg-Gly-Lys (SEQ ID NO: 11) at the C-terminus of the heavy chain. Pharmaceutical compositions comprising the antibody (or mixture of antibodies) and methods of using the antibody are also provided.

An "anti-sclerostin antibody" or an "antibody that binds to sclerostin" is an antibody that binds to sclerostin of SEQ ID NO: 1 or portions thereof. Recombinant human sclerostin/SOST is commercially available from, e.g., R&D Systems (Minneapolis, Minn., USA; 2006 Catalog #1406-ST-025). U.S. Pat. Nos. 6,395,511 and 6,803,453, and U.S. Patent Publication Nos. 2004/0009535 and 2005/0106683 refer to anti-sclerostin antibodies generally. Examples of sclerostin antibodies suitable for use in the context of the invention also are described in U.S. Patent Publication Nos. 2007/0110747 and 2007/0072797, which are hereby incorporated by reference. Additional information regarding materials and methods for generating sclerostin antibodies can be found in U.S. Patent Publication No. 20040158045 (hereby incorporated by reference).

The term "antibody" refers to an intact immunoglobulin molecule (including polyclonal, monoclonal, chimeric, humanized, and/or human versions having full length heavy and/or light chains).

"Specifically binds" as used herein means that the antibody preferentially binds the antigen over other proteins. In some embodiments, "specifically binds" means the antibody has a higher affinity for the antigen than for other proteins. Antibodies that specifically bind an antigen may have a binding affinity for the antigen of less than or equal to $1 \times 10^{-7}$ M, less than or equal to $2 \times 10^{-7}$ M, less than or equal to $3 \times 10^{-7}$ M, less than or equal to $4 \times 10^{-7}$ M, less than or equal to $5 \times 10^{-7}$ M, less than or equal to $6 \times 10^{-7}$ M, less than or equal to $7 \times 10^{-7}$ M, less than or equal to $8 \times 10^{-7}$ M, less than or equal to $9 \times 10^{-7}$ M, less than or equal to $1 \times 10^{-8}$ M, less than or equal to $2 \times 10^{-8}$ M, less than or equal to $3 \times 10^{-8}$ M, less than or equal to $4 \times 10^{-8}$ M, less than or equal to $5 \times 10^{-8}$ M, less than or equal to $6 \times 10^{-8}$ M, less than or equal to $7 \times 10^{-8}$ M, less than or equal to $8 \times 10^{-8}$ M, less than or equal to $9 \times 10^{-8}$ M, less than or equal to $1 \times 10^{-9}$ M, less than or equal to $2 \times 10^{-9}$ M, less than or equal to $3 \times 10^{-9}$ M, less than or equal to $4 \times 10^{-9}$ M, less than or equal to $5 \times 10^{-9}$ M, less than or equal to $6 \times 10^{-9}$ M, less than or equal to $7 \times 10^{-9}$ M, less than or equal to $8 \times 10^{-9}$ M, less than or equal to $9\times10^{-9}$ M, less than or equal to $1\times10^{-10}$ M, less than or equal to $2\times10^{-10}$ M, less than or equal to $3\times10^{-10}$ M, less than or equal to $4\times10^{-10}$ M, less than or equal to $5\times10^{-10}$ M, less than or equal to $6\times10^{-10}$ M, less than or equal to $7\times10^{-10}$ M, less than or equal to $8\times10^{-10}$ M, less than or equal to $9\times10^{-10}$ M, less than or equal to $1\times10^{-11}$ M, less than or equal to $2\times10^{-11}$ M, less than or equal to $3\times10^{-11}$ M, less than or equal to $4\times10^{-11}$ M, less than or equal to $5\times10^{-11}$ M, less than or equal to $6\times10^{-11}$ M, less than or equal to $7\times10^{-11}$ M, less than or equal to $8\times10^{-11}$ M, less than or equal to $9\times10^{-11}$ M, less than or equal to $1\times10^{-12}$ M, less than or equal to $2\times10^{-12}$ M, less than or equal to $3\times10^{-12}$ M, less than or equal to $4\times10^{-12}$ M, less than or equal to $5\times10^{-12}$ M, less than or equal to $6\times10^{-12}$ M, less than or equal to $7\times10^{-12}$ M, less than or equal to $8\times10^{-12}$ M, or less than or equal to $9\times10^{-12}$ M.

In some or any embodiments, the antibody binds to sclerostin of SEQ ID NO: 1, or a naturally occurring variant thereof, with an affinity (Kd) of less than or equal to $1\times10^{-7}$ M, less than or equal to $1\times10^{-8}$ M, less than or equal to $1\times10^{-9}$ M, less than or equal to $1\times10^{-10}$ M, less than or equal to $1\times10^{-11}$ M, or less than or equal to $1\times10^{-12}$ M. Affinity is determined using a variety of techniques, an example of which is an affinity ELISA assay. In various embodiments, affinity is determined by a BIAcore assay. In various embodiments, affinity is determined by a kinetic method. In various embodiments, affinity is determined by an equilibrium/solution method. U.S. Patent Publication No. 2007/0110747 (the disclosure of which is incorporated herein by reference) contains additional description of affinity assays suitable for determining the affinity (Kd) of an antibody for sclerostin.

In some or any embodiments, the antibody (or antibody fragments thereof) binds to a sclerostin polypeptide comprising the amino acid sequence set forth in SEQ ID NO: 1 and binds a region of sclerostin comprising the sequence of SEQ ID NO: 5 (CGPARLLPNAIGRGKWWRPSGPDFRC; corresponding to amino acids 86-111 of SEQ ID NO: 1). This region is also referred to herein as the "loop 2" region of sclerostin. Regions of sclerostin outside of the loop 2 region are defined herein as "non-loop 2 regions." Alternatively or in addition, the anti-sclerostin antibody binds to a sclerostin polypeptide comprising amino acids 57-146 of SEQ ID NO: 1. Alternatively or in addition, the anti-sclerostin antibody binds to a sclerostin polypeptide comprising amino acids 89-103 of SEQ ID NO: 1 and/or amino acids 137-151 of SEQ ID NO: 1. In some or any embodiments, the sclerostin polypeptide that is a fragment of full length sclerostin retains the tertiary structure of the corresponding polypeptide region of human sclerostin of SEQ ID NO: 1.

In some or any embodiments, the anti-sclerostin antibody described herein preferably modulates sclerostin function in the cell-based assay described in U.S. Patent Publication No. 2007/0110747 and/or the in vivo assay described in U.S. Patent Publication No. 20070110747 and/or bind to one or more of the epitopes described in U.S. Patent Publication No. 2007/0110747 and/or cross-block the binding of one of the antibodies described in U.S. Patent Publication No. 2007/0110747 and/or are cross-blocked from binding sclerostin by one of the antibodies described in U.S. Patent Publication No. 2007/0110747 (incorporated by reference in its entirety and for its description of assays for characterizing an anti-sclerostin antibody).

"CDR" refers to the complementarity determining region within antibody variable sequences. There are three CDRs in each of the variable regions of the heavy chain and the light chain, which are designated CDR1, CDR2 and CDR3, for each of the variable regions. The term "set of six CDRs" as used herein refers to a group of three CDRs that occur in the light chain variable region and heavy chain variable region, which are capable of binding the antigen. The exact boundaries of CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Chothia and coworkers (Chothia & Lesk, J. Mol. Biol. 196:901-917 (1987) and Chothia et al., Nature 342:877-883 (1989)) found that certain sub-portions within Kabat CDRs adopt nearly identical peptide backbone conformations, despite having great diversity at the level of amino acid sequence. These sub-portions were designated as L1, L2 and L3 or H1, H2 and H3 where the "L" and the "H" designates the light chain and the heavy chains regions, respectively. These regions may be referred to as Chothia CDRs, which have boundaries that overlap with Kabat CDRs. Other boundaries defining CDRs overlapping with the Kabat CDRs have been described by Padlan (FASEB J. 9:133-139 (1995)) and MacCallum (J Mol Biol 262(5):73245 (1996)). Still other CDR boundary definitions may not strictly follow one of the above systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although preferred embodiments use Kabat or Chothia defined CDRs.

CDRs are obtained by, e.g., constructing polynucleotides that encode the CDR of interest. Such polynucleotides are prepared, for example, by using the polymerase chain reaction to synthesize the variable region using mRNA of antibody-producing cells as a template (see, for example, Larrick et al., Methods: A Companion to Methods in Enzymology, 2:106 (1991); Courtenay-Luck, "Genetic Manipulation of Monoclonal Antibodies," in Monoclonal Antibodies Production, Engineering and Clinical Application, Ritter et al. (eds.), page 166, Cambridge University Press (1995); and Ward et al., "Genetic Manipulation and Expression of Antibodies," in Monoclonal Antibodies: Principles and Applications, Birch et al., (eds.), page 137, Wiley-Liss, Inc. (1995)).

In various aspects, the antibody comprises at least one CDR sequence having at least 75% identity (e.g., at least 75%, 80%, 85%, 90%, 95% or 100% identity) to a CDR selected from CDR-H1, CDR-H2, CDR-H3, CDR-L1, CDR-L2, and CDR-L3 wherein CDR-H1 has the sequence given in SEQ ID NO: 2, CDR-H2 has the sequence given in SEQ ID NO: 3, CDR-H3 has the sequence given in SEQ ID NO: 4, CDR-L1 has the sequence given in SEQ ID NO: 5, CDR-L2 has the sequence given in SEQ ID NO: 6 and CDR-L3 has the sequence given in SEQ ID NO: 7. The anti-sclerostin antibody, in various aspects, comprises two of the CDRs or six of the CDRs.

In a preferred embodiment, the anti-sclerostin antibody comprise a set of six CDRs as follows: CDR-H1 of SEQ ID NO: 2, CDR-H2 of SEQ ID NO: 3, CDR-H3 of SEQ ID NO: 4, CDR-L1 of SEQ ID NO: 5, CDR-L2 of SEQ ID NO: 6 and CDR-L3 of SEQ ID NO: 7.

In some or any embodiments, the antibody comprises a light chain variable region comprising an amino acid sequence having at least 75% identity (e.g., at least 75%, 80%, 85%, 90%, 95% or 100% identity) to the amino acid sequence set forth in SEQ ID NO: 9 and a heavy chain variable region comprising an amino acid sequence having at least 75% identity (e.g., at least 75%, 80%, 85%, 90%, 95% or 100% identity) to the amino acid sequence set forth in SEQ ID NO: 10. In various aspects, the difference in the sequence compared to SEQ ID NO: 9 or 10 lies outside the CDR region in the corresponding sequences. In some or any embodiments, the antibody comprises a light chain variable region comprising an amino acid sequence set forth in SEQ ID NO: 9 and a heavy chain variable region comprising an amino acid sequence set forth in SEQ ID NO: 10.

In some or any embodiments the anti-sclerostin antibody comprises all or part of a heavy chain (e.g., two heavy chains) comprising an amino acid sequence having at least 75% identity (e.g., at least 75%, 80%, 85%, 90%, 95% or 100% identity) to the amino acid sequence set forth in SEQ ID NO: 16 and all or part of a light chain (e.g., two light chains) comprising an amino acid sequence having at least 75% identity (e.g., at least 75%, 80%, 85%, 90%, 95% or 100% identity) to the amino acid sequence set forth in SEQ ID NO 12.

The antibody comprises a heavy chain comprising the amino acid sequence Pro-Ala-Arg-Gly (SEQ ID NO: 8) at the C-terminus of the heavy chains. In some embodiments, the C-terminus of both heavy chains of the antibody comprises the amino acid sequence Pro-Ala-Arg-Gly (SEQ ID NO: 8). In some embodiments, the antibody comprises a first heavy chain comprising the amino acid sequence Pro-Ala-Arg-Gly (SEQ ID NO: 8) and a second heavy chain comprising a wild-type amino acid sequence. The antibody, in various aspects, comprises the light chain amino acid sequence set forth in SEQ ID NO: 12 and the heavy chain amino acid sequence set forth in SEQ ID NO: 13.

Alternatively, in some or any embodiments, the antibody comprises a sequence of amino acids comprising Pro-Ala-Arg-Gly-Lys (SEQ ID NO: 11) at the C-terminus of a heavy chain, optionally at the C-terminus of both heavy chains. In some embodiments, the antibody comprises a first heavy chain comprising the amino acid sequence Pro-Ala-Arg-Gly-Lys (SEQ ID NO: 11) and a second heavy chain comprising a wild-type amino acid sequence (i.e., without the C-terminal Pro-Ala-Arg-Gly-Lys (SEQ ID NO: 11)). The antibody, in various aspects, comprises the light chain amino acid sequence set forth in SEQ ID NO: 12 and the heavy chain amino acid sequence set forth in SEQ ID NO: 14.

Examples of other anti-sclerostin antibodies include, but are not limited to, the anti-sclerostin antibodies disclosed in International Patent Publication Nos. WO 2008/092894, WO 2008/115732, WO 2009/056634, WO 2009/047356, WO 2010/100200, WO 2010/100179, WO 2010/115932, and WO 2010/130830 (each of which is incorporated by reference herein in its entirety).

It will be understood by one skilled in the art that some proteins, such as antibodies, may undergo a variety of posttranslational modifications. The type and extent of these modifications often depends on the host cell line used to express the protein as well as the culture conditions. Such modifications may include variations in glycosylation, methionine oxidation, diketopiperizine formation, aspartate isomerization and asparagine deamidation. A frequent modification is the loss of a carboxy-terminal basic residue (such as lysine or arginine) due to the action of carboxypeptidases (as described in Harris, R J. *Journal of Chromatography* 705:129-134, 1995).

Other modifications include hydroxylation of proline and lysine, phosphorylation of hydroxyl groups of seryl or threonyl residues, methylation of the $\alpha$-amino groups of lysine, arginine, and histidine side chains (T. E. Creighton, Proteins: Structure and Molecular Properties, W. H. Freeman & Co., San Francisco, pp. 79-86 [1983], entirely incorporated by reference), acetylation of the N-terminal amine, and amidation of any C-terminal carboxyl group.

In some or any embodiments, the C-terminus of the heavy chain of the antibody, comprising the amino acid sequence Pro-Ala-Arg-Gly (SEQ ID NO: 8), is amidated. In some or any embodiments, both heavy chains of the antibody comprise the amino acid sequence Pro-Ala-Arg-Gly (SEQ ID NO: 8) and both heavy chains are amidated. In some embodiments, the glycine is amidated. Amidation can occur, e.g., as described in Prigg, S. T. et al., "New insights into copper monooxygenases and peptide amidation: structure, mechanism and function", Cell. Mol. Life Sci. 57 (2000) 1236-1259. The enzyme peptidylglycine $\alpha$-amidating monooxygenase (PAM) can catalyze the amidation of glycine. PAM has two active domains, peptidylglycine $\alpha$-hydroxylating monooxygenase (PHM) and peptidyl-$\alpha$-hydroxylglycine $\alpha$-amidating lyase (PAL). PHM catalyzes the conversion of peptidylglycine (along with ascorbate and oxygen) to peptidyl $\alpha$-hydroxylglycine (along with semidehydrogenascorbate and water). In turn, PAL catalyzes the conversion of peptidyl $\alpha$-hydroxylglycine to an amidated peptide (and glyoxylate).

Amidation of an antibody can be controlled by altering certain conditions during the cell culture process. For example, copper (e.g., in ferric ammonium citrate) and/or oxygen levels may be used to influence amidation levels. It is contemplated that increasing copper concentration (e.g., in the media) or oxygen availability (e.g., during culturing) may increase amidation by impacting the activity of an enzyme such as PHM.

Pharmaceutical Compositions

The disclosure provides a pharmaceutical composition comprising a population of the antibody described herein together with a pharmaceutically effective diluent, carrier, solubilizer, emulsifier, preservative, and/or adjuvant. Pharmaceutical compositions of the invention include, but are not limited to, liquid, frozen, and lyophilized compositions.

The disclosure also provides a pharmaceutical composition comprising a mixture of antibodies that specifically bind to sclerostin of SEQ ID NO: 1 and a pharmaceutically acceptable carrier, wherein about 3-5% of the antibodies in the composition are a population of antibodies described herein (e.g., antibodies comprising set of six CDRs set forth in SEQ ID NOs: 2-7 and having a heavy chain (or two heavy chains) comprising the amino acid sequence Pro-Ala-Arg-Gly (SEQ ID NO: 8) at the C-terminus of the heavy chain(s)). The disclosure also contemplates compositions comprising alternative amounts (e.g., 5-10%, 1-3%, 3-15%, 2-10%, 4-20%, 1-5%) of the population of antibodies described herein (e.g., antibodies comprising set of six CDRs set forth in SEQ ID NOs: 2-7 and having a heavy chain (or two heavy chains) comprising the amino acid sequence Pro-Ala-Arg-Gly (SEQ ID NO: 8) at the C-terminus of the heavy chain(s)).

In some embodiments, less than 70% of the antibodies of the population (e.g., about 69%, about 68%, about 67%, about 66%, about 65%, about 64%, about 63%, about 62%, about 61%, about 60%, about 59%, about 58%, about 57%, about 56%, about 55%, about 54%, about 53%, about 52%, about 51%, about 50%, about 49%, about 48%, about 47%, about 46%, about 45%, about 44%, about 43%, about 42%, about 41%, about 40%, about 39%, about 38%, about 37%, about 36%, about 35%, about 34%, about 33%, about 32%, about 31%, about 30%, about 29%, about 28%, about 27%, about 26%, about 25%, about 24%, about 23%, about 22%, about 21%, about 20%, about 19%, about 18%, about 17%, about 16%, about 15%, about 14%, bout 13%, about 12%, about 11%, about 10%, about 9%, about 8%, about 7%, about 6%, about 5%, about 4%, about 3%, about 2%, about 1% or less) comprise a heavy chain comprising a C-terminal Pro-Ala-Arg-Gly (SEQ ID NO: 8) sequence, which is optionally amidated. In some embodiments, less than 35% (e.g., about 34%, about 33%, about 32%, about 31%, about 30%, about 29%, about 28%, about 27%, about 26%, about 25%, about 24%, about 23%, about 22%, about 21%, about 20%, about 19%, about 18%, about 17%, about 16%, about 15%, about 14%, bout 13%, about 12%, about 11%, about 10%, about 9%, about 8%, about 7%, about 6%, about 5%, about 4%, about 3%, about 2%, about 1% or less) of the antibodies of the population comprise a C-terminal Pro-Ala-Arg-Gly (SEQ ID NO: 8) sequence on both heavy chains, where both heavy chains are optionally amidated. It is also contemplated that both heavy chains comprise the C-terminal Pro-Ala-Arg-Gly (SEQ ID NO: 8) sequence but only one of the chains is amidated. In some embodiments, less than 35% (e.g., about 34%, about 33%, about 32%, about 31%, about 30%, about 29%, about 28%, about 27%, about 26%, about 25%, about 24%, about 23%, about 22%, about 21%, about 20%, about 19%, about 18%, about 17%, about 16%, about 15%, about 14%, bout 13%, about 12%, about 11%, about 10%, about 9%, about 8%, about 7%, about 6%, about 5%, about 4%, about 3%, about 2%, about 1% or less) of the antibodies in the composition comprise a C-terminal Pro-Ala-Arg-Gly (SEQ ID NO: 8) sequence that is not amidated. In some embodiments, about 33% of antibodies of the population comprise a C-terminal Pro-Ala-Arg-Gly (SEQ ID NO: 8) sequence that is amidated, about 33% of the antibodies of the population comprise C-terminal Pro-Ala-Arg-Gly (SEQ ID NO: 8) sequences on both heavy chains which are both amidated, and about 33% of the antibodies of the population comprise heavy chain(s) with a C-terminal Pro-Ala-Arg-Gly (SEQ ID NO: 8) sequence but which are not amidated.

In some embodiments, the pharmaceutical composition contains formulation materials for modifying, maintaining or preserving, for example, the pH, osmolarity, viscosity, clarity, color, isotonicity, odor, sterility, stability, rate of dissolution or release, adsorption or penetration of the composition. In such embodiments, suitable formulation materials include, but are not limited to, amino acids (such as glycine, glutamine, asparagine, arginine, proline, or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. See, REMINGTON'S PHARMACEUTICAL SCIENCES, 18th Edition, (A. R. Genrmo, ed.), 1990, Mack Publishing Company.

Selection of the particular formulation materials described herein may be driven by, for example, the intended route of administration, delivery format and desired dosage. See, for example, REMINGTON'S PHARMACEUTICAL SCIENCES, supra. The primary vehicle or carrier in a pharmaceutical composition may be either aqueous or non-aqueous in nature. For example, a suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles. In specific embodiments, pharmaceutical compositions comprise Tris buffer of about pH 7.0-8.5, or acetate buffer of about pH 4.0-5.5, and may further include sorbitol or a suitable substitute therefor. In certain embodiments, the composition may be prepared for storage by mixing the selected composition having the desired degree of purity with optional formulation agents (REMINGTON'S PHARMACEUTICAL SCIENCES, supra) in the form of a lyophilized cake or an aqueous solution. Further, in some embodiments, the antibody or fragment may be formulated as a lyophilizate using appropriate excipients such as sucrose.

The pharmaceutical compositions of the invention can be selected for parenteral delivery. Alternatively, the compositions may be selected for inhalation or for delivery through the digestive tract, such as orally. Preparation of such pharmaceutically acceptable compositions is within the skill of the art. The formulation components are present preferably in concentrations that are acceptable to the site of administration. In certain embodiments, buffers are used to maintain the composition at physiological pH or at a slightly lower pH, typically within a pH range of from about 5 to about 8.

When parenteral administration is contemplated, the therapeutic compositions for use in this invention may be provided in the form of a pyrogen-free, parenterally acceptable aqueous solution comprising the desired antibody or fragment in a pharmaceutically acceptable vehicle. A particularly suitable vehicle for parenteral injection is sterile distilled water in which the antibody or fragment is formulated as a sterile, isotonic solution, properly preserved. In certain embodiments, implantable drug delivery devices may be used to introduce the desired antibody or fragment.

In some or any embodiments, the pharmaceutical composition described herein comprises a calcium salt, an acetate buffer, a polyol and a surfactant. Exemplary calcium salts include, but are not limited to, calcium acetate, calcium carbonate and calcium chloride. In some embodiments, the calcium salt is at a concentration of at least 0.5 mM, at least 1 mM, at least 2 mM, at least 3 mM, at least 4 mM, at least 5 mM, at least 6 mM, at least 7 mM, at least 8 mM, at least 9 mM or at least 10 mM. In certain embodiments, the concentration of calcium salt is not greater than 11 mM, no greater than 12 mM, no greater than 13 mM, no greater than 14 mM, no greater than 15 mM, no greater than 16 mM, no greater than 17 mM, no greater than 18 mM, no greater than 19 mM, no greater than 20 mM, no greater than 21 mM, no greater than 22 mM, no greater than 23 mM, no greater than 24 mM, or no greater than 25 mM. Any range featuring a combination of the foregoing endpoints is contemplated, including but not limited to from about 0.5 mM to about 10 mM, about 5 mM to about 10 mM, or about 5 mM to about 15 mM.

In some embodiments, the pharmaceutical composition comprises an acetate buffer (e.g., sodium acetate) having a concentration ranging from about 0.1 mM to about 1000 mM (1 M). In some embodiments, the concentration of the acetate buffer is at least 5 mM, at least 6 mM, at least 7 mM, at least 8 mM, at least 9 mM, at least 10 mM, at least 15 mM, at least 60 mM, at least 70 mM, at least 80 mM, at least 90 mM, at least 100 mM, at least 200 mM, at least 500 mM, at least 700 mM, or at least 900 mM. In some embodiments, the concentration of the acetate buffer is no greater than 10 mM, no greater than 15 mM, no greater than 20 mM, no greater than 25 mM, no greater than 30 mM, no greater than 35 mM, no greater than 40 mM, no greater than 45 mM, no greater than 50 mM, no greater than 55 mM, no greater than 60 mM, no greater than 65 mM, no greater than 70 mM, no greater than 75 mM, no greater than 80 mM, no greater than 85 mM, no greater than 90 mM, no greater than 95 mM or no greater than 100 mM. Any range featuring a combination of the foregoing endpoints is contemplated, including but not limited to from about 5 mM to about 15 mM, or from about 5 mM to about 10 mM or from about 10 mM to about 25 mM. The buffer is preferably added to a concentration that maintains pH around 5-6 or 5-5.5 or 4.5-5.5. When the calcium salt in the formulation is calcium acetate, in some embodiments, the total concentration of acetate is about 10 mM to about 55 mM, or about 20 mM to about 40 mM.

In some aspects, the pharmaceutical composition comprises a total concentration of acetate that is at least about 10 mM, at least about 15 mM, at least about 20 mM, at least about 25 mM, at least about 30 mM, at least about 35 mM, at least about 40 mM, 45 mM, or 50 mM. In some embodiments, the concentration of acetate is no greater than about 30 mM, 35 mM, 40 mM, 45 mM, 50 mM, 55 mM, 60 mM, 65 mM, 70 mM, 75 mM, 80 mM, 85 mM, or 90 mM. Any range featuring a combination of the foregoing endpoints is contemplated, including but not limited to: about 10 mM to about 50 mM, about 20 mM to about 50 mM, about 20 mM to about 40 mM, about 30 mM to about 50 mM, or about 30 mM to about 75 mM. In some embodiments, the calcium salt is calcium acetate and the acetate buffer is sodium acetate. By way of nonlimiting example, a solution containing 10 mM calcium acetate will have 20 mM acetate anion and 10 mM of calcium cation, because of the divalent nature of the calcium cation, while a solution containing 10 mM sodium acetate will have 10 mM sodium cation and 10 mM acetate anion.

In some embodiments, the total concentration of ions (cations and anions) in solution is at least 10 mM, at least about 15 mM, at least about 20 mM, at least about 25 mM, at least about 30 mM, at least about 35 mM, at least about 40 mM, at least about 45 mM, at least about 50 mM, at least about 55 mM, at least about 60 mM, at least about 65 mM, at least about 70 mM, at least about 75 mM, at least about 80 mM, or at least about 85 mM. In some embodiments, the total concentration of ions is no greater than about 30 mM, no greater than about 35 mM, no greater than about 40 mM, no greater than about 45 mM, no greater than about 50 mM, no greater than about 55 mM, no greater than about 60 mM, no greater than about 65 mM, no greater than about 70 mM, no greater than about 75 mM, no greater than about 80 mM, no greater than about 85 mM, no greater than about 90 mM, no greater than about 95 mM, no greater than about 100 mM, no greater than about 110 mM, no greater than about 120 mM, no greater than about 130 mM, no greater than about 140 mM, no greater than about 150 mM, no greater than about 160 mM, no greater than about 170 mM, no greater than about 180 mM, no greater than about 190 mM or no greater than about 200 mM. Any range featuring a combination of the foregoing endpoints is contemplated, including but not limited to: about 30 mM to about 60 mM, or about 30 mM to about 70 mM, or about 30 mM to about 80 mM, or about 40 mM to about 150 mM, or about 50 mM to about 150 mM. By way of nonlimiting example, a solution of 10 mM calcium acetate will have a 30 mM total concentration of ions (10 mM cations and 20 mM anions).

In some or any embodiments, the pharmaceutical composition comprises a polyol. Polyols encompass a class of excipients that includes sugars (e.g. mannitol, sucrose, sorbitol) and other polyhydric alcohols (e.g., glycerol and propylene glycol). Exemplary polyols include, but are not limited to, propylene glycol, glycerin (glycerol), threose, threitol, erythrose, erythritol, ribose, arabinose, arabitol, lyxose, maltitol, sorbitol, sorbose, glucose, mannose, mannitol, levulose, dextrose, maltose, trehalose, fructose, xylitol, inositol, galactose, xylose, fructose, sucrose, 1,2,6-hexanetriol and the like. Higher order sugars include, but are not limited to, dextran, propylene glycol, or polyethylene glycol. Reducing sugars such as fructose, maltose or galactose oxidize more readily than do non-reducing sugars. Additional examples of sugar alcohols are glucitol, maltitol, lactitol or iso-maltulose. Additional exemplary lyoprotectants include glycerin and gelatin, and the sugars mellibiose, melezitose, raffinose, mannotriose, and stachyose. Examples of reducing sugars include glucose, maltose, lactose, maltulose, iso-maltulose and lactulose. Examples of non-reducing sugars include non-reducing glycosides of polyhydroxy compounds selected from sugar alcohols and other straight chain polyalcohols. Monoglycosides include compounds obtained by reduction of disaccharides such as lactose, maltose, lactulose and maltulose.

In some or any embodiments, the pharmaceutical composition comprises a polyol at a concentration ranging from about 0% to about 40% w/v. In some or any embodiments, the compositions comprise a polyol at concentration of at least 0.5, at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 30, or at least 40% w/v. In some or any embodiments, the composition comprises a polyol at a concentration of about 1, 2, 3, 4, 5, 6, 7, 8, 9% to about 10% w/v. In some or any embodiments, the composition comprises a polyol at a concentration of about 2% to about 6% w/v. In some or any embodiments, the composition comprises a polyol at a concentration of about 4% w/v. In some or any embodiments, the composition comprises a polyol at about 6% w/v.

In some or any embodiments, the pharmaceutical composition comprises a surfactant. Exemplary surfactants include, but are not limited to, anionic, cationic, nonionic, zwitterionic, and amphoteric surfactants including surfactants derived from naturally-occurring amino acids. Anionic surfactants include, but are not limited to, sodium lauryl sulfate, dioctyl sodium sulfosuccinate and dioctyl sodium sulfonate, chenodeoxycholic acid, N-lauroylsarcosine sodium salt, lithium dodecyl sulfate, 1-octanesulfonic acid sodium salt, sodium cholate hydrate, sodium deoxycholate, and glycodeoxycholic acid sodium salt. Cationic surfactants include, but are not limited to, benzalkonium chloride or benzethonium chloride, cetylpyridinium chloride monohydrate, and hexadecyltrimethylammonium bromide. Zwitterionic surfactants include, but are not limited to, CHAPS, CHAPSO, SB3-10, and SB3-12. Non-ionic surfactants include, but are not limited to, digitonin, Triton X-100, Triton X-114, TWEEN-20, and TWEEN-80. In another embodiment, surfactants include, but are not limited to, lauromacrogol 400, polyoxyl 40 stearate, polyoxyethylene hydrogenated castor oil 10, 40, 50 and 60, glycerol monostearate, polysorbate 20, polysorbate 40, polysorbate 60, polysorbate 65 and polysorbate 80, soy lecithin and other phospholipids such as DOPC, DMPG, DMPC, and DOPG; sucrose fatty acid ester, methyl cellulose and carboxymethyl cellulose. In some or any embodiments, the surfactant is polysorbate 20.

Surfactants may be included in the compositions either individually or as a mixture in different ratios. In some or any embodiments, the composition comprises a surfactant at a concentration of about 0% to about 5% w/v (e.g., about 0.001, about 0.002, about 0.005, about 0.007, about 0.01, about 0.05, about 0.1, about 0.2, about 0.3, about 0.4, about 0.5, about 0.6, about 0.7, about 0.8, about 0.9, about 1.0, about 1.5, about 2.0, about 2.5, about 3.0, about 3.5, about 4.0, or about 4.5% w/v). In some or any embodiments, the composition comprises a surfactant at a concentration of about 0.001% to about 0.5% w/v. In some or any embodiments, the composition comprises a surfactant at a concentration of about 0.004, about 0.005, about 0.007, about 0.01, about 0.05, or about 0.1% w/v to about 0.2% w/v. In some or any embodiments, the composition comprises a surfactant at a concentration of about 0.01% to about 0.1% w/v.

In some or any embodiments, the pharmaceutical composition comprises 55 mM acetate, 13 mm calcium, 6.0% (w/v) sucrose, 0.006% (w/v) polysorbate 20, pH 5.2.

Additional pharmaceutical compositions will be evident to those skilled in the art, including formulations involving antigen binding proteins in sustained- or controlled-delivery formulations. Techniques for formulating a variety of other sustained- or controlled-delivery means, such as liposome carriers, bio-erodible microparticles or porous beads and depot injections, are also known to those skilled in the art. See, for example, International Patent Application No. PCT/US93/00829, which is incorporated by reference and describes controlled release of porous polymeric microparticles for delivery of pharmaceutical compositions. Sustained-release preparations may include semipermeable polymer matrices in the form of shaped articles, e.g., films, or microcapsules. Sustained release matrices may include polyesters, hydrogels, polylactides (as disclosed in U.S. Pat. No. 3,773,919 and European Patent Application Publication No. EP058481, each of which is incorporated by reference), copolymers of L-glutamic acid and gamma ethyl-L-glutamate (Sidman et al., 1983, Biopolymers 2:547-556), poly (2-hydroxyethyl-methacrylate) (Langer et al., 1981, J. Biomed. Mater. Res. 15:167-277 and Langer, 1982, Chem. Tech. 12:98-105), ethylene vinyl acetate (Langer et al., 1981, supra) or poly-D(−)-3-hydroxybutyric acid (European Patent Application Publication No. EP133988). Sustained release compositions may also include liposomes that can be prepared by any of several methods known in the art. See, e.g., Eppstein et al., 1985, Proc. Natl. Acad. Sci. U.S.A. 82:3688-3692; European Patent Application Publication Nos. EP036676; EP088046 and EP143949, incorporated by reference.

Pharmaceutical compositions used for in vivo administration are typically provided as sterile preparations. Sterilization can be accomplished by filtration through sterile filtration membranes. When the composition is lyophilized, sterilization using this method may be conducted either prior to or following lyophilization and reconstitution. Compositions for parenteral administration can be stored in lyophilized form or in a solution. Parenteral compositions generally are placed into a container having a sterile access port, for example, an intravenous solution bag or vial having a stopper pierceable by a hypodermic injection needle.

Free amino acids can be used in antibody or fragment formulations in accordance with various embodiments of the invention as bulking agents, stabilizers, and antioxidants, as well as other standard uses. Lysine, proline, serine, and alanine can be used for stabilizing proteins in a formulation. Glycine is useful in lyophilization to ensure correct cake structure and properties. Arginine may be useful to inhibit protein aggregation, in both liquid and lyophilized formulations. Methionine is useful as an antioxidant.

Embodiments of antibody formulations may further comprise one or more antioxidants. To some extent deleterious oxidation of proteins can be prevented in pharmaceutical formulations by maintaining proper levels of ambient oxygen and temperature and by avoiding exposure to light. Antioxidant excipients can be used as well to prevent oxidative degradation of proteins. Among useful antioxidants in this regard are reducing agents, oxygen/free-radical scavengers, and chelating agents. Antioxidants for use in therapeutic protein formulations in accordance with the invention preferably are water-soluble and maintain their activity throughout the shelf life of a product. EDTA is a preferred antioxidant in accordance with the invention in this regard.

Formulations in accordance with the invention may include metal ions that are protein co-factors and that are necessary to form protein coordination complexes, such as zinc necessary to form certain insulin suspensions. Metal ions also can inhibit some processes that degrade proteins. However, metal ions also catalyze physical and chemical processes that degrade proteins.

Magnesium ions (10-120 mM) can be used to inhibit isomerization of aspartic acid to isoaspartic acid. $Ca^{+2}$ ions (up to 100 mM) can increase the stability of human deoxyribonuclease. $Mg^{+2}$, $Mn^{+2}$, and $Zn^{+2}$, however, can destabilize rhDNase. Similarly, $Ca^{+2}$ and $Sr^{+2}$ can stabilize Factor VIII, it can be destabilized by $Mg^{+2}$, $Mn^{+2}$ and $Zn^{+2}$, $Cu^{+2}$ and $Fe^{+2}$, and its aggregation can be increased by $Al^{+3}$ ions.

Embodiments of the antibody formulations can further comprise one or more preservatives.

Once the pharmaceutical composition has been formulated, it may be stored in sterile vials as a solution, suspension, gel, emulsion, solid, crystal, or as a dehydrated or lyophilized powder. Such formulations may be stored either in a ready-to-use form or in a form (e.g., lyophilized) that is reconstituted prior to administration. The invention also provides kits for producing a single-dose administration unit. The kits of the invention may each contain both a first container having a dried protein and a second container having an aqueous formulation. In certain embodiments of this invention, kits containing single and multi-chambered pre-filled syringes (e.g., liquid syringes and lyosyringes) are provided.

The therapeutically effective amount of an antibody-containing pharmaceutical composition to be employed will depend, for example, upon the therapeutic context and objectives. One skilled in the art will appreciate that the appropriate dosage levels for treatment will vary depending, in part, upon the molecule delivered, the indication(s) for which the antibody is being used, the route of administration, and the size (body weight, body surface or organ size) and/or condition (the age and general health) of the patient.

Stability

The terms "stability" and "stable" as used herein in the context of a composition comprising an antibody (or antigen binding fragment thereof) refer to the resistance of the antibody (or antigen binding fragment thereof) in the composition to aggregation, degradation or fragmentation under given manufacture, preparation, transportation and/or storage conditions. Antibody formulations comprising a high degree of stability demonstrate enhanced reliability and safety and, as such, are advantageous for clinical use.

Antibody stability in a composition is optionally assessed by examining a desired parameter of the antibody in the composition (e.g., aggregation, degradation of heavy and/or light chains, chemical modification, etc.) over time. In this regard, a parameter is typically examined at an initial time point (TO) and an assessment time point (T1), optionally while exposing the antibody to any of a number of environmental conditions, and compared. An initial time point can be, for instance, the time that the antibody is first formulated in a composition or first examined for quality (i.e., examined to determine whether the antibody composition meets regulatory or manufacturing specifications with respect to aggregation or degradation). An initial time point also can be the time at which the antibody is reformulated in a composition (e.g., reformulated at a higher or lower concentration compared to an initial preparation). An assessment time point is, in various embodiments, about 1 week (or about 2 weeks, or about 3 weeks, or about 4 weeks, or about 5 weeks, or about 6 weeks, or about 7 weeks, or about 8 weeks, or about 10 weeks, or about 3 months, or about 6 months or about 1 year) after the initial time point. The desired parameter (e.g., aggregation or degradation) of the antibody or fragment thereof in the composition can be assessed under a variety of storage conditions, such as temperatures of −30° C., 4° C., 20° C. or 40° C., shaking, pH, storage in different container materials (e.g., glass vials, pre-filled syringes, etc.), and the like.

Exemplary methods for determining the degree of aggregation, and/or types and/or sizes of aggregates present in a composition comprising the antibody include, but are not limited to, size exclusion chromatography (SEC), high performance size exclusion chromatography (HPSEC), static light scattering (SLS), Fourier Transform Infrared Spectroscopy (FTIR), circular dichroism (CD), urea-induced protein unfolding techniques, intrinsic tryptophan fluorescence, differential scanning calorimetry, and 1-anilino-8-naphthalene-sulfonic acid (ANS) protein binding techniques. Size exclusion chromatography (SEC) may be performed to separate molecules on the basis of their size, by passing the molecules over a column packed with the appropriate resin, the larger molecules (e.g. aggregates) will elute before smaller molecules (e.g. monomers). The molecules are generally detected by UV absorbance at 280 nm and may be collected for further characterization. High pressure liquid chromatographic columns are often utilized for SEC analysis (HPSEC). Alternatively, analytical ultracentrifugation (AUC) may be utilized. AUC is an orthogonal technique which determines the sedimentation coefficients of macromolecules in a liquid sample. Like SEC, AUC is capable of separating and detecting antibody fragments/aggregates from monomers and is further able to provide information on molecular mass. Antibody aggregation in a composition may also be characterized by particle counter analysis using a coulter counter or by turbidity measurements using a turbidimeter. Turbidity is a measure of the amount by which the particles in a solution scatter light and, thus, may be used as a general indicator of protein aggregation. In addition, non-reducing polyacrylamide gel electrophoresis (PAGE) or capillary gel electrophoresis (CGE) may be used to characterize the aggregation and/or fragmentation state of antibodies or antibody fragments in a composition.

Exemplary methods for determining antibody degradation include, but are not limited to, size-exclusion chromatography (SEC), sodium dodecyl sulfate-polyacrylamide gel electrophoresis (SDS-PAGE) and capillary electrophoresis with SDS (CE-SDS) and reversed phase HPLC with in-line MS detection.

In various embodiments, less than 5% of the antibody described herein in the composition is in aggregate form under conditions of interest. For instance, less than 4%, or less than 3%, or less than 2%, or less than 1% of the antibody in the composition is in aggregate form after storage at −30° C., 4° C., 20° C. or 40° C. for a period of about 1 week (or about 2 weeks, or about 3 weeks, or about 4 weeks, or about 5 weeks, or about 6 weeks, or about 7 weeks, or about 8 weeks, or about 10 weeks, or about 3 months, or about 6 months or about 1 year). In some embodiments, less than 5% (or less than 4% or less than 3% or less than 2% or less than 1% or less) of the antibody described herein in the composition is in aggregate form after storage for two weeks at about 4° C.

For example at least 85% (or at least 90%, or at least 91%, or at least 92%, or at least 93%, or at least 94%, or at least 95%, or at least 96%, or at least 97%, or at least 98%, or at least 99%) of antibody in a composition optionally is present in non-aggregate (i.e., monomeric) form after storage at −30° C., 4° C., 20° C. or 40° C. for a period of about 1 week (or about 2 weeks, or about 3 weeks, or about 4 weeks, or about 5 weeks, or about 6 weeks, or about 7 weeks, or about 8 weeks, or about 10 weeks, or about 3 months, or about 6 months or about 1 year). In some embodiments, at least 85% (or at least 90%, or at least 91%, or at least 92%, or at least 93%, or at least 94%, or at least 95%, or at least 96%, or at least 97%, or at least 98%, or at least 99% or more) of the antibody is present in the composition in non-aggregate form after two weeks of storage at about 4° C. In some embodiments, at least 99% of the antibody is present in the composition in non-aggregate form after storage for two weeks at about 4° C. for two weeks and/or at least 95% of antibody present in the composition is in non-aggregate form after storage for two weeks at 40° C.

In various embodiments, less than 5% of the antibody described herein in the composition is degraded. For instance, less than 4%, or less than 3%, or less than 2%, or less than 1% or less of the antibody in the composition is degraded under conditions of interest. For example, optionally at least 85% (or at least 90%, or at least 91%, or at least 92%, or at least 93%, or at least 94%, or at least 95%, or at least 96%, or at least 97%, or at least 98%, or at least 99%) of the antibody is intact (i.e., not degraded) in a composition stored at about −30° C., about 4° C., about 20° C. or about 40° C. for a period of about 1 week (or about 2 weeks, or about 3 weeks, or about 4 weeks, or about 5 weeks, or about 6 weeks, or about 7 weeks, or about 8 weeks, or about 10 weeks, or about 3 months, or about 6 months or about 1 year). In some aspects, at least 85% (or at least 90%, or at least 91%, or at least 92%, or at least 93%, or at least 94%, or at least 95%, or at least 96%, or at least 97%, or at least 98%, or at least 99% or more) of the antibody is intact (i.e., non-degraded) after storage in a composition at about 4° C. for a period of two weeks. In some embodiments, at least 99% of the antibody remains intact when stored in a composition at about 4° C. for two weeks and/or at least 95% remains intact when stored in a composition at about 40° C. for two weeks.

Functional or activity stability of the antibody in a composition also is contemplated herein. Assays for detecting and/or quantifying, e.g., antibody binding to a target or sclerostin neutralization are known in the art. Optionally, the antibody demonstrates about 50-100% activity under conditions of interest compared to the activity of the antibody at the initial time point. For example, the antibody retains a level of activity of between about 60-90% or 70-80% compared to the activity the initial time point. Accordingly, functional stability of the antibody includes retention of activity of at least about 50%, 55%, 60%, 65%, 70%, 75%, 80%, 85%, 90%, 95% or 100% and can include activity measurements greater than 100% such as 105%, 110%, 115%, 120%, 125% or 150% or more compared to the activity at the initial time point.

Viscosity

In some embodiments, the viscosity of a composition comprising one or more of the antibodies described herein is determined. The term "viscosity" as used herein refers to "absolute viscosity." Absolute viscosity, sometimes called dynamic or simple viscosity, is the product of kinematic viscosity and fluid density (Absolute Viscosity=Kinematic Viscosity×Density). The dimension of kinematic viscosity is $L^2/T$ where L is a length and T is a time. Commonly, kinematic viscosity is expressed in centistokes (cSt). The SI unit of kinematic viscosity is $mm^2/s$, which is 1 cSt. Absolute viscosity is expressed in units of centipoise (cP). The SI unit of absolute viscosity is the millipascal-second (mPa-s), where 1 cP=1 mPa-s.

The viscosity of a composition can be measured hours (e.g., 1-23 hours), days (e.g., 1-10 days), weeks (e.g., 1-5 weeks), months (e.g., 1-12 months), or years (e.g., 1-2 years, 1-3 years) after the addition of the antibody to the composition. Viscosity measurements may be made at a storage or administration temperature, e.g. 2-8° C. or 25° C. (room temperature). In some embodiments, absolute viscosity of the liquid or reconstituted liquid composition at the storage and/or administration temperature is 15 cP or less, or 14, 13, 12, 11, 10, 9, 8, 7, 6, 5, or 4 cP or less. In some embodiments, absolute viscosity of the liquid or reconstituted liquid composition is 6 cP or less.

In some embodiments, the viscosity of the antibody composition is measured prior to and after the addition of antibody. Methods of measuring viscosity are well known in the art and include, for example, using a capillary viscometer, or a cone-plate rheometer. Any method may be used provided the same method is used to compare the test and reference formulations.

Therapeutic Methods

The antibody and pharmaceutical compositions described herein are useful for treating or preventing bone-related disorders, such as bone-related disorders associated with abnormal osteoblast or osteoclast activity. In some embodiments, the antibody is administered to a subject suffering from a bone related disorder selected from the group consisting of achondroplasia, cleidocranial dysostosis, enchondromatosis, fibrous dysplasia, Gaucher's Disease, hypophosphatemic rickets, Marfan's syndrome, multiple hereditary exotoses, neurofibromatosis, osteogenesis imperfecta, osteopetrosis, osteopoikilosis, sclerotic lesions, pseudoarthrosis, pyogenic osteomyelitis, periodontal disease, anti-epileptic drug induced bone loss, primary and secondary hyperparathyroidism, familial hyperparathyroidism syndromes, weightlessness induced bone loss, osteoporosis in men, postmenopausal bone loss, osteoarthritis, renal osteodystrophy, infiltrative disorders of bone, oral bone loss, osteonecrosis of the jaw, juvenile Paget's disease, melorheostosis, metabolic bone diseases, mastocytosis, sickle cell anemia/disease, organ transplant related bone loss, kidney transplant related bone loss, systemic lupus erythematosus, ankylosing spondylitis, epilepsy, juvenile arthritides, thalassemia, mucopolysaccharidoses, Fabry Disease, Turner Syndrome, Down Syndrome, Klinefelter Syndrome, leprosy, Perthe's Disease, adolescent idiopathic scoliosis, infantile onset multi-system inflammatory disease, Winchester Syndrome, Menkes Disease, Wilson's Disease, ischemic bone disease (such as Legg-Calve-Perthes disease and regional migratory osteoporosis), anemic states, conditions caused by steroids, glucocorticoid-induced bone loss, heparin-induced bone loss, bone marrow disorders, scurvy, malnutrition, calcium deficiency, osteoporosis, osteopenia, alcoholism, chronic liver disease, postmenopausal state, chronic inflammatory conditions, rheumatoid arthritis, inflammatory bowel disease, ulcerative colitis, inflammatory colitis, Crohn's disease, oligomenorrhea, amenorrhea, pregnancy-related bone loss, diabetes mellitus, hyperthyroidism, thyroid disorders, parathyroid disorders, Cushing's disease, acromegaly, hypogonadism, immobilization or disuse, reflex sympathetic dystrophy syndrome, regional osteoporosis, osteomalacia, bone loss associated with joint replacement, HIV associated bone loss, bone loss associated with loss of growth hormone, bone loss associated with cystic fibrosis, chemotherapy-associated bone loss, tumor-induced bone loss, cancer-related bone loss, hormone ablative bone loss, multiple myeloma, drug-induced bone loss, anorexia nervosa, disease-associated facial bone loss, disease-associated cranial bone loss, disease-associated bone loss of the jaw, disease-associated bone loss of the skull, bone loss associated with aging, facial bone loss associated with aging, cranial bone loss associated with aging, jaw bone loss associated with aging, skull bone loss associated with aging, and bone loss associated with space travel.

In some embodiments, the antibodies described herein are useful for improving outcomes in orthopedic procedures, dental procedures, implant surgery, joint replacement, bone grafting, bone cosmetic surgery and bone repair such as fracture healing, nonunion healing, delayed union healing and facial reconstruction. A composition comprising one or more antibodies may be administered before, during and/or after the procedure, replacement, graft, surgery or repair.

In some embodiments, the antibodies described herein are useful for the treatment of any fracture comprising a gap between two segments of bone (e.g., a gap of at least about 1 mm between two segments of bone). In some or any embodiments, the gap is at least about 2 mm, at least about 3 mm, at least about 4 mm, at least about 5 mm, at least about 6 mm, at least about 7 mm, at least about 8 mm, at least about 9 mm, or at least about 1 cm or more. In some or any embodiments, the gap is about 5 mm to 1 cm, or up to 1 cm. The terms "bone gap defect" and "segmental skeletal defect" are used synonymously herein and refer to a gap between two segments of bone (e.g., a gap of at least 1 mm).

Exemplary bone gap defects include, but are not limited to, a comminuted fracture, a non-union fracture, a segmental skeletal defect, surgically created bone defects, surgically treated bone defects, and bone defects created from traumatic injury to the bone or disease (including, but not limited to, arthritis, tumor removal (resection) or infection removal). In some or any embodiments, the bone gap defect is produced by removal of infected sections of bone or the removal of cancer from the bone due to bone cancers including, but not limited to, osteosarcoma, Ewing's sarcoma, chondrosarcoma, malignant fibrous histiocytoma, fibrosarcoma, and chordoma. In some or any embodiments, the bone gap defect is a developmental deformity, e.g., due to a genetic defect.

In some or any embodiments, the bone gap defect is produced by removal of sections of bone containing a benign tumor. Exemplary benign bone tumors include, but are not limited to, osteoma, osteoid osteoma, osteoblastoma, osteochondroma, enchondroma, chondromyxoid fibroma, aneurysmal bone cyst, unicameral bone cyst, fibrous dysplasia of bone and giant cell tumor of the bone.

Administration of the antibody enhances or accelerates bone gap defect healing, thereby "treating" the bone gap defect. "Enhancing" bone healing means mediating a level of bone healing beyond (i.e., greater than) the level of bone healing experienced in subjects (e.g., mammals, such as humans) not administered the sclerostin inhibitor (i.e., control subjects). Bone healing is evidenced by, for example, bridging status, improved bone volume, improved bone mineral content and density within the fracture gap (i.e., formation of bridging bone), mature bone callus, improved bone strength (optionally accompanied by a medically-acceptable level of bone stiffness), or improved patient use of the affected area. By "improved" is meant an increase or decrease (as desired) in the measured parameter. The increase can be a return, in whole or in part, of the measured parameter to baseline level (e.g., the level prior to the bone gap defect), to values provided in normative databases used in the art, or to the contralateral functional level (e.g., return, in whole or in part, to the functional capabilities of, for example, the contralateral limb). In some cases, the increase can be an improvement beyond baseline level. If desired, the measured parameters in patients administered one or more doses of the antibody can be compared to the same parameters in fracture patients (optionally age and gender matched) not administered the antibody to further analyze the efficacy of the methods described herein.

Formation of bridging bone, bone mineral content and bone density, and/or mature boney callus at the site of bone defect may be measured using radiography (e.g., radiographic absorptiometry), single- and/or dual-energy X-ray absorptiometry, quantitative computed tomography (QCT), ultrasonography, radiography (e.g., radiographic absorptiometry), and magnetic resonance imaging. In some embodiments, the antibody may be administered at a dose and for a time period effective to increase bridging bone formation, formation of bony callus, or bone density (or volume) at the defect site by at least about 5% (about 6%, about 7%, about 8%, or about 9%). In some embodiments, bridging bone formation, formation of bony callus, or bone density at the defect site is increased by at least about 10% (e.g., at least about 10%, at least about 12%, at least about 15%, at least about 18%, at least about 20%, or at least about 22%). In other embodiments, bridging bone formation, formation of bony callus, or bone density at the defect site is increased by the sclerostin inhibitor at least about 25% (e.g., at least about 26% or at least about 28%). In yet other embodiments, bridging bone formation, formation of bony callus, or bone density at the defect site is increased at least about 30% (e.g., at least about 32%, at least about 35%, at least about 38%, or at least about 40%) or at least about 50% (e.g., at least about 60%, at least about 70%, at least about 80%, at least about 90%, or about 100%). The increase or re-establishment of bridging bone formation can be determined at 1 week, 2 weeks, 3 weeks, or 4 weeks following the initial administration of antibody. Alternatively, the bone density level can be determined after the treatment period ends (e.g., 1 week, 2 weeks, 3 weeks, or 4 weeks after the treatment period ends). In one aspect, the method reduces the amount of time required to establish a desired level of bone formation, bone volume, bony callus, or bone density (e.g., any percent increase in bone formation, bone mineral density, bony callus, or bone volume described herein) compared to age and gender-matched patients that do not receive the antibody, thereby reducing recovery time for a subject. For example, in one embodiment, the antibody reduces the amount of time required to increase bone density or volume at the defect site at least about 10% (e.g., at least about 20%, at least about 25%, at least about 30%, at least about 35%, at least about 40%, at least about 45%, or at least about 50%).

The antibody need not cure the subject of the disorder or completely protect against the onset of a bone-related disorder to achieve a beneficial biological response. The antibody may be used prophylactically, meaning to protect, in whole or in part, against a bone-related disorder or symptom thereof. The antibody also may be used therapeutically to ameliorate, in whole or in part, a bone-related disorder or symptom thereof, or to protect, in whole or in part, against further progression of a bone-related disorder or symptom thereof. Indeed, the materials and methods of the invention are particularly useful for increasing bone mineral density, and optionally maintaining the increased bone mineral density over a period of time.

In some embodiments, one or more administrations of an antibody described herein are carried out over a therapeutic period of, for example, about 1 week to about 18 months (e.g., about 1 month to about 12 months, about 1 month to about 9 months or about 1 month to about 6 months or about 1 month to about 3 months). In some embodiments, a subject is administered one or more doses of a antibody described herein over a therapeutic period of, for example about 1 month to about 12 months (52 weeks) (e.g., about 2 months, about 3 months, about 4 months, about 5 months, about 6 months, about 7 months, about 8 months, about 9 months, about 10 months, or about 11 months).

In addition, it may be advantageous to administer multiple doses of the antibody or space out the administration of doses, depending on the therapeutic regimen selected for a particular subject. In some embodiments, the antibody or fragment thereof is administered periodically over a time period of one year (12 months, 52 weeks) or less (e.g., 9 months or less, 6 months or less, or 3 months or less). In this regard, the antibody or fragment thereof is administered to the human once every about 3 days, or about 7 days, or 2 weeks, or 3 weeks, or 4 weeks, or 5 weeks, or 6 weeks, or 7 weeks, or 8 weeks, or 9 weeks, or 10 weeks, or 11 weeks, or 12 weeks, or 13 weeks, or 14 weeks, or 15 weeks, or 16 weeks, or 17 weeks, or 18 weeks, or 19 weeks, or 20 weeks, or 21 weeks, or 22 weeks, or 23 weeks, or 6 months, or 12 months.

In some embodiments, one or more doses of the antibody are administered in an amount and for a time effective to increase bone mineral density or treat a bone disorder associated with decreased bone mineral density. In various embodiments, one or more doses comprising from about 50 milligrams to about 1,000 milligrams of the antibody are administered per week to a subject (e.g., a human subject). For example, a dose of antibody can comprise at least about 5 mg, 15 mg, 25 mg, 50 mg, about 60 mg, about 70 mg, about 80 mg, about 90 mg, about 100 mg, about 120 mg, about 150 mg, about 200 mg, about 210 mg, about 240 mg, about 250 mg, about 280 mg, about 300 mg, about 350 mg, about 400 mg, about 420 mg, about 450 mg, about 500 mg, about 550 mg, about 600 mg, about 650 mg, about 700 mg, about 750 mg, about 800 mg, about 850 mg, about 900 mg, about 950 mg or up to about 1,000 mg of antibody. Ranges between any and all of these endpoints are also contemplated, e.g. about 50 mg to about 80 mg, about 70 mg to about 140 mg, about 70 mg to about 270 mg, about 75 mg to about 100 mg, about 100 mg to about 150 mg, about 140 mg to about 210 mg, or about 150 mg to about 200 mg, or about 180 mg to about 270 mg, or about 280 to about 410 mg. The dose is administered at any interval, such as multiple times a week (e.g., twice or three times per week), once a week, once every two weeks, once every three weeks, or once every four weeks. In some or any embodiments, a dose of antibody ranging from about 120 mg to about 210 mg is administered twice a week. In some or any embodiments, a dose of about 140 mg of the antibody is administered twice a week. In various aspects, a dose of about 210 mg of antibody is administered once a month.

In some embodiments, the one or more doses of antibody can comprise between about 0.1 to about 50 milligrams (e.g., between about 5 and about 50 milligrams), or about 1 to about 100 milligrams, of antibody per kilogram of body weight (mg/kg). For example, the dose of antibody may comprise at least about 0.1 mg/kg, 0.5 mg/kg, 1 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 20 mg/kg, about 25 mg/kg, about 26 mg/kg, about 27 mg/kg, about 28 mg/kg, about 29 mg/kg, about 30 mg/kg, about 31 mg/kg, about 32 mg/kg, about 33 mg/kg, about 34 mg/kg, about 35 mg/kg, about 36 mg/kg, about 37 mg/kg, about 38 mg/kg, about 39 mg/kg, about 40 mg/kg, about 41 mg/kg, about 42 mg/kg, about 43 mg/kg, about 44 mg/kg, about 45 mg/kg, about 46 mg/kg, about 47 mg/kg, about 48 mg/kg, or about 49 mg/kg, or about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, or up to about 100 mg/kg. Ranges between any and all of these endpoints are also contemplated, e.g., about 1 mg/kg to about 3 mg/kg, about 1 mg/kg to about 5 mg/kg, about 1 mg/kg to about 8 mg/kb, about 3 mg/kg to about 8 mg·kg, about 1 mg/kg to about 10 mg/kg, about 1 mg/kg to about 20 mg/kg, about 1 mg/kg to about 40 mg/kg, about 5 mg/kg to about 30 mg/kg, or about 5 mg/kg to about 20 mg/kg.

Monitoring Therapy

Antibody-mediated increases in bone mineral content or bone density may be measured using single- and dual-energy X-ray absorptiometry, ultrasound, computed tomography, radiography, and magnetic resonance imaging. The amount of bone mass may also be calculated from body weights or by using other methods (see Guinness-Hey, Metab. Bone Dis. Relat. Res., 5:177-181 (1984)). Animal models are used in the art for testing the effect of the pharmaceutical compositions and methods on, for example, parameters of bone loss, bone resorption, bone formation, bone strength, or bone mineralization that mimic conditions of human disease such as osteoporosis and osteopenia.

Examples of such models include the ovariectomized rat model (Kalu, Bone and Mineral, 15:175-192 (1991); Frost and Jee, Bone and Mineral, 18:227-236 (1992); and Jee and Yao, J. Musculoskel. Neuron. Interact., 1:193-207 (2001)). The methods for measuring antibody activity described herein also may be used to determine the efficacy of other sclerostin inhibitors.

In humans, bone mineral density can be determined clinically using dual x-ray absorptiometry (DXA) of, for example, the hip and spine. Other techniques include quantitative computed tomography (QCT), ultrasonography, single-energy x-ray absorptiometry (SXA), and radiographic absorptiometry. Common central skeletal sites for measurement include the spine and hip; peripheral sites include the forearm, finger, wrist and heel. Except for ultrasonography, the American Medical Association notes that BMD techniques typically involve the use of x-rays and are based on the principle that attenuation of the radiation depends on thickness and composition of the tissues in the radiation path. All techniques involve the comparison of results to a normative database.

Alternatively, a physiological response to one or more anti-sclerostin antibodies can be gauged by monitoring bone marker levels. Bone markers are products created during the bone remodeling process and are released by bone, osteoblasts, and/or osteoclasts. Fluctuations in bone resorption and/or bone formation "marker" levels imply changes in bone remodeling/modeling. The International Osteoporosis Foundation (IOF) recommends using bone markers to monitor bone density therapies (see, e.g., Delmas et al., Osteoporos Int., Suppl. 6:52-17 (2000), incorporated herein by reference). Markers indicative of bone resorption (or osteoclast activity) include, for example, C-telopeptide (e.g., C-terminal telopeptide of type 1 collagen (CTX) or serum cross-linked C-telopeptide), N-telopeptide (N-terminal telopeptide of type 1 collagen (NTX)), deoxypyridinoline (DPD), pyridinoline, urinary hydroxyproline, galactosyl hydroxylysine, and tartrate-resistant acid phosphatase (e.g., serum tartrate-resistant acid phosphatase isoform 5b). Bone formation/mineralization markers include, but are not limited to, bone-specific alkaline phosphatase (BSAP), peptides released from N- and C-terminal extension of type I procollagen (P1NP, PICP), and osteocalcin (OstCa). Several kits are commercially-available to detect and quantify markers in clinical samples, such as urine and blood.

Combination Therapy

Treatment of a pathology by combining two or more agents that target the same pathogen or biochemical pathway or biological process sometimes results in greater efficacy and diminished side effects relative to the use of a therapeutically relevant dose of each agent alone. In some cases, the efficacy of the drug combination is additive (the efficacy of the combination is approximately equal to the sum of the effects of each drug alone), but in other cases the effect is synergistic (the efficacy of the combination is greater than the sum of the effects of each drug given alone). As used herein, the term "combination therapy" means that two or more agents are delivered in a simultaneous manner, e.g., concurrently, or wherein one of the agents is administered first, followed by the second agent, e.g., sequentially.

In some embodiments, the antibody is administered along with a standard of care therapeutic for the treatment of decreased bone mineral density (i.e., the antibody and standard of care therapeutic are part of the same treatment plan). As used herein, the term "standard of care" refers to a treatment that is generally accepted by clinicians for a certain type of patient diagnosed with a type of illness. In some embodiments, the antibody is administered along with a second bone-enhancing agent useful for the treatment of decreased bone mineral density or bone defect. In some embodiments, the bone-enhancing agent is selected from the group consisting of an anti-resorptive agent, a bone-forming agent (i.e., anabolic), an estrogen receptor modulator (including, but not limited to, raloxifene, bazedoxifene and lasofoxifene) and a drug that has an inhibitory effect on osteoclasts. In some embodiments, the second bone-enhancing agent is selected from the group consisting of a bisphosphonate (including, but not limited to, alendronate sodium (FOSAMAX®), risedronate, ibandronate sodium (BONIVA®) and zoledronic acid (RECLAST®)); an estrogen or estrogen analogue; an anti-RANK ligand (RANKL) inhibitor, such as an anti-RANKL antibody (e.g., denosumab, PROLIA®); vitamin D, or a vitamin D derivative or mimic thereof; a calcium source, a cathepsin-K (cat-K) inhibitor (e.g. odanacatib), Tibolone, calcitonin or a calcitriol; and hormone replacement therapy. In some embodiments, the second bone-enhancing agent includes, but is not limited to, parathyroid hormone (PTH) or a peptide fragment thereof, PTH-related protein (PTHrp), bone morphogenetic protein, osteogenin, NaF, a PGE2 agonist, a statin, strontium ranelate, and a sclerostin inhibitor (e.g., an anti-sclerostin antibody described in, for example, U.S. Pat. Nos. 7,592,429 or 7,872,106). In some embodiments, the second bone-enhancing agent is Forteo® (Teriparatide), Preotact®, or Protelos®. In some embodiments, the second bone-enhaiving agent comprises a bone morphogenetic protein (e.g., BMP-1, BMP-2, BMP-3, BMP-4, BMP-5, BMP-6, BMP-7, BMP-8, BMP-9, BMP-10, BMP-11, BMP-12, BMP-13, BMP-14 and/or BMP-15).

In some embodiments, the combination therapy employing an antibody described herein may precede or follow administration of additional therapeutic(s) (e.g., second bone-enhancing agent) by intervals ranging from minutes to weeks to months. For example, separate modalities are administered within about 24 hours of each other, e.g., within about 6-12 hours of each other, or within about 1-2 hours of each other, or within about 10-30 minutes of each other. In some situations, it may be desirable to extend the time period for treatment significantly, where several days (2, 3, 4, 5, 6 or 7 days) to several weeks (1, 2, 3, 4, 5, 6, 7 or 8 weeks) lapse between the respective administrations of different modalities. Repeated treatments with one or both agents/therapies of the combination therapy is specifically contemplated.

Maintenance Therapeutic Regimen

Also contemplated is the use of a second bone-enhancing agent and/or antibody described herein in a maintenance regimen to, e.g., prevent or slow the loss of bone mineral density. In this regard, a method or use described herein optionally comprises administering one or more amounts of a second bone-enhancing agent effective to maintain bone mineral density for a maintenance period of about 1 week to about 5 years after the treatment period with the antibody has ended. For example, in some embodiments, a method or use described herein comprises the administration of a second bone-enhancing agent to the subject for a maintenance period of about at least about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 3 months, about 13 weeks, about 14 weeks, about 15 weeks, about 16 weeks, about 4 months, about 17 weeks, about 18 weeks, about 19 weeks, about 20 weeks, about 5 months, about 21 weeks, about 22 weeks, about 23 weeks, about 24 weeks, about 6 months, about 25 weeks, about 26 weeks, about 27 weeks, about 28 weeks, about 7 months, about 29 weeks, about 30 weeks, about 31 weeks or longer (e.g., about 8 months, about 9 months, about 10 months, about 11 months, about 1 year, about 15 months, about 18 months, about 2 years, about 3 years, about 4 years, about 5 years or longer (e.g., over the lifetime of the subject). In some embodiments, the maintenance period is about 6-12 weeks. In some embodiments, the maintenance period is about 4-12 weeks, or about 1-3 months. In some embodiments, the maintenance period is about 12-20 weeks, or about 3-5 months. In some embodiments, the maintenance period is about 20-32 weeks, or about 5-8 months. In some embodiments, the maintenance period is about 24-36 weeks, or about 6-9 months. In some embodiments, the maintenance period is about 1 year, about 2 years, about 3 years, about 4 years, about 5 years or longer. "Maintaining" bone mineral density includes maintaining similar levels of bone mineral density parameters experienced in the subject that received the antibody treatment.

Kits

A pharmaceutical composition comprising one or more antibodies described herein may be placed within containers (e.g., vials or syringes), along with packaging material that provides instructions regarding the use of such pharmaceutical compositions. Generally, such instructions will include a tangible expression describing the antibody concentration, as well as within certain embodiments, relative amounts of excipient ingredients or diluents (e.g., water, saline or PBS) that may be necessary to reconstitute the pharmaceutical composition.

EXAMPLES

Example 1—Analysis of Romosozumab PARG (SEQ ID NO: 8) C-Terminal Variant

Figure 3:
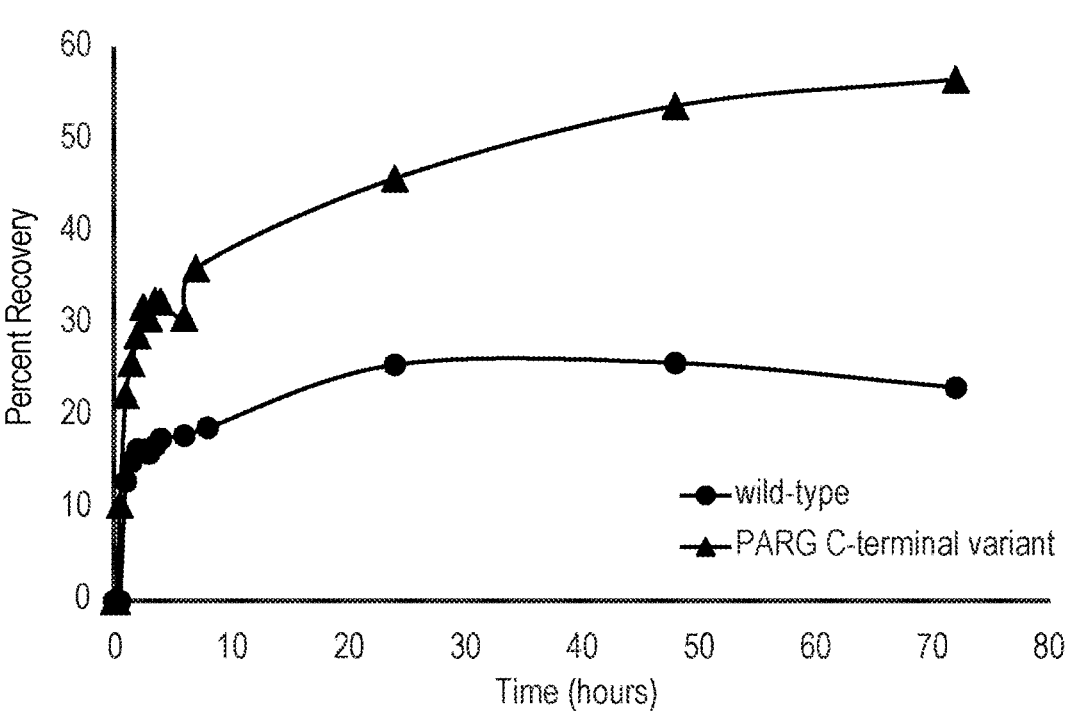

Wild-type romosozumab and a romosozumab PARG (SEQ ID NO: 8) C-terminal variant were digested by Lys-C and analyzed by LC/MS peptide mapping. The UV profiles of these two constructs were compared side by side (FIG. 3). It was determined that wild-type romosozumab and the romosozumab PARG (SEQ ID NO: 8) C-terminal variant have a similar peak eluting at 37.7 minutes but wild-type romosozumab was determined to have a mass of 659.3 Da and the romosozumab PARG (SEQ ID NO: 8) C-terminal variant was determined to have a mass of 886.7 Da. The majority of lysine (K) variants of romosozumab (PGK) was thought to be removed from the process. The presence of a significant amount of the amidated form of the romosozumab PARG (SEQ ID NO: 8) C-terminal variant (828.6 Da peak) confirms that the amidation efficiency is sequence dependent when compared to the wild-type romosozumab PG sequence.

Figure 1:
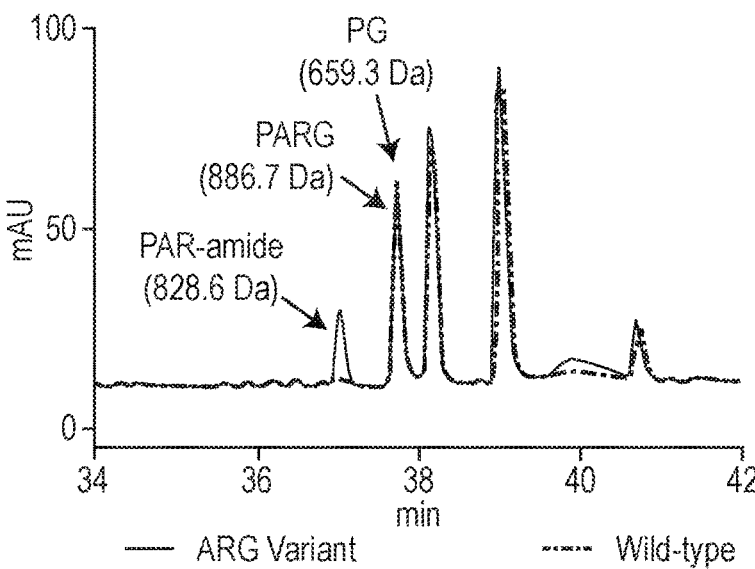
FIG. 1 is a graph showing the zoomed in UV profile of wild-type romosozumab (dotted line) overlaid with and the romosozumab PARG (SEQ ID NO: 8) variant (solid line) that has been digested by Lys-C and analyzed by LC/MS peptide mapping.
Figure 2:
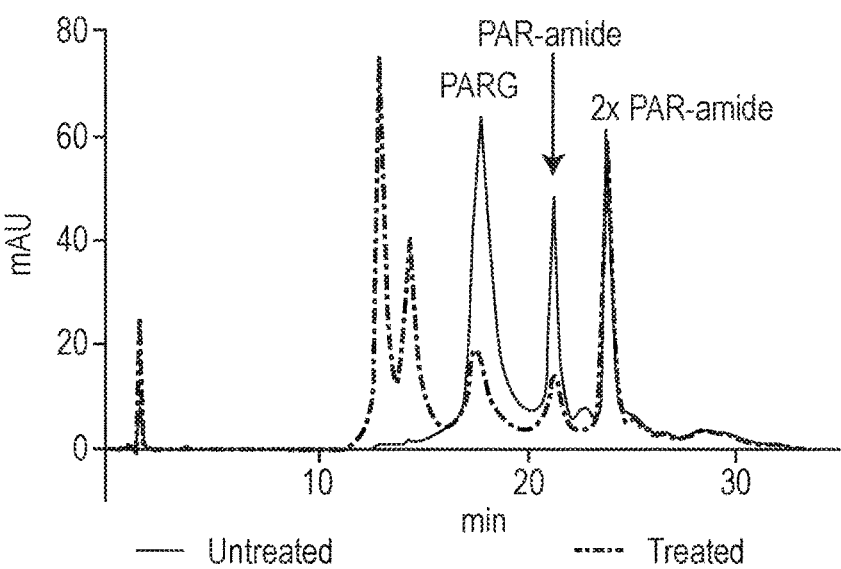
FIG. 2 is a graph showing the cation exchange (CEX) profile of carboxypeptidase treated romosozumab PARG (SEQ ID NO: 8) variant (dotted line) overlaid with untreated romosozumab PARG (SEQ ID NO: 8) variant (solid line).

Next, the PARG (SEQ ID NO: 8) C-terminal variant was then treated with carboxypeptidase (CP-B), analyzed by CEX-HPLC method and compared with the PARG (SEQ ID NO: 8) C-terminal variant control which was not treated by the CP-B. There is a significant shift post treatment for the peaks eluting at 17.5 mins and 21 mins, but not for the peak at 24 mins (FIG. 2). It is contemplated that the 24 min peak is the doubly amidated form, which is protected from proteolytic degradation.

Example 2—C-Terminal Variant Enrichment

Purification or enrichment for different romosozumab species from a composition comprising wild-type romosozumab and the romosozumab PARG (SEQ ID NO: 8) C-terminal variant is achieved by Cation Exchange Chromatography (CEX) fractionation. CEX separates proteins based on differences in their surface charges. At a set pH, positively charged variants of wild-type romosozumab are separated on a cation-exchange column (e.g., Dionex Pro Pac WCX-10 analytical column, 2.0 mm×250 mm) and eluted using a salt gradient (e.g., Mobile Phase A: 10:90 (v/v) ACN, 19 mM MES pH 6.2; Mobile Phase B: 10:90 (v/v) ACN, 19 mM MES, 250 mM NaCl, pH 6.2). The different C-terminal variants of romosozumab are charged differently and the more positively charged variant elutes later in CEX. Thus, the elution order is: PG (wild-type), P-amide (amidated proline of wild-type), PARG (SEQ ID NO: 8) variant, and PAR-amide. The fraction collector can be programmed to collect CEX eluents containing different variants at different elution times.

Example 3—Analysis of Romosozumab PARG (SEQ ID NO: 8) C-Terminal Variant Aggregation Without being bound to any particular theory, it is contemplated that because the PARG (SEQ ID NO: 8) C-terminal variant is highly charged, such forms would repel non-amidated forms in the compositions, thus reducing aggregation in the composition.

Romosozumab PARG (SEQ ID NO: 8) C-terminal variant protein A pool was analyzed side by side with wild-type romosozumab protein A pool using SEC-HPLC, a size exclusion HPLC method that separates protein based on differences in their hydrodynamic volume (Table 1).

TABLE 1

| Molecule | % HMW |
|---|---|
| AMG785 ARG ProA pool | 3.4% |
| AMG785 WT ProA pool | 7.2% |

The data demonstrated that romosozumab PARG (SEQ ID NO: 8) C-terminal variant has less high molecular weight species as compared to the wild-type romosozumab.

Example 4—Viscosity Analysis of Romosozumab PARG (SEQ ID NO: 8) C-Terminal Variant Antibody solutions containing romosozumab PARG (SEQ ID NO: 8) C-terminal variant or wild-type romosozumab are measured using a cone and plate. The solutions are concentrated up to 120 mg/mL according to approximate volume depletion, and final concentrations are determined (±10%) using the proteins absorbance at 280 nm (after dilution to end up within 0.1-1 absorbance units (AU)) and a protein specific extinction coefficient. Viscosity analysis is performed on a Brookfield LV-DVIII cone and plate instrument (Brookfield Engineering, Middleboro, MA, USA) using a CP-40 spindle and sample cup or an ARES-G2 rheometer (TA Instruments, New Castle, DE, USA) using a TA Smart Swap 2 degree cone/plate spindle. All measurements are performed at 25° C. and controlled by a water bath attached to the sample cup. Multiple viscosity measurements were collected, manually within a defined torque range (10-90%) by increasing the RPM of the spindle. Measurements are averaged in order to report one viscosity value per sample to simplify the resulting comparison chart.

Example 5—Solubility Analysis of Romosozumab PARG (SEQ ID NO: 8) C-Terminal Variant To determine the impact of the amino acid variation of romosozumab PARG (SEQ ID NO: 8) variant as compared to the wild type romosozumab on solubility upon subcutaneous (SC) injection, a dialysis solubility assay was performed on both wild type and PARG (SEQ ID NO: 8) C-terminal variant romosozumab in parallel. This screen entails dialyzing a sample of the romosozumab PARG (SEQ ID NO: 8) C-terminal variant and a sample of the wild-type romosozumab into a solution that simulates the pH and ionic strength of the SC space and monitoring the solubility and physical stability of the antibody in these conditions over a short time period. Samples were formulated at ~63 mg/mL in formulation buffer (pH 5.2). Then each sample was injected into a dialysis cassette and dialyzed into a PBS buffer to mimic the SC space. Visual observations were made 24 hours after initial dialysis. Wild-type romosozumab typically shows precipitation after 24 hours.

The results show that both molecules precipitate in this analysis but the PARG (SEQ ID NO: 8) C-terminal variant precipitates less and at a slower rate. This suggests that the variant is more resistant to precipitation than wild type, although the variant does not abolish precipitation completely.

Example 6—Diffusion Analysis of Romosozumab PARG (SEQ ID NO: 8) C-Terminal Variant To determine the impact of the amino acid variation of romosozumab PARG (SEQ ID NO: 8) C-terminal variant as compared to the wild type romosozumab on diffusion from the subcutaneous (SC) space, an assay was performed using Scissor (Pion Inc., Billerica, MA). This assay entails injecting the samples (the romosozumab PARG (SEQ ID NO: 8) C-terminal variant or wild-type romosozumab) at ~70 mg/mL into a simulated SC space comprised of a collagen and hyaluronic acid matrix. The antibody is able to diffuse out of this matrix through a dialysis membrane into a reservoir of carbonate buffer at pH 7.4. Time points were collected for up to 3 days and each time point was assayed for protein concentration by RP-HPLC. The protein concentration vs. time curves generated simulate the diffusion rates from the SC space. In addition, precipitation in the SC matrix is monitored with visual inspection.

Both the wild type and PARG (SEQ ID NO: 8) C-terminal variant romosozumab were tested in the Scissor as described above. The results shown in FIG. 3 indicate that wild type romosozumab diffuses from the simulated SC space at a much lower rate and more wild type romosozumab is retained at the simulated injection site than PARG (SEQ ID NO: 8) C-terminal variant romosozumab.

Example 7—FcRn Binding

FcRn, the neonatal Fc receptor, is an MHC class I-like heterodimer composed of a transmembrane a chain (homologous to MHC class-I like molecules) and a β2 microglobulin light chain. FcRn binds to the interface between $C_H2$ and $C_H3$ domains of IgG heavy chains in the Fc region of the IgG molecule under mildly acidic conditions (~pH 6) and releases it at neutral pH (~7.4). By this highly pHdependent interaction, FcRn mediates IgG homeostasis in human adults by maintaining serum IgG levels.

A competitive binding assay, the AlphaScreen® binding assay (PerkinElmer, San Jose, CA), was used to assess the binding of the Fc domain of wild-type romosozumab and romosozumab PARG (SEQ ID NO: 8) C-terminal variant to FcRn. The assay is a bead based amplified luminescent proximity homogeneous assay ("Alpha") that detects bimolecular interactions. The assay contains two bead types, an acceptor bead and a donor bead. The acceptor beads are coated with a hydrogel that contains thioxene derivatives, as well as nickel chelate which binds to the histidine domain of histidine labeled FcRn (FcRn-His). The donor beads are coated with a hydrogel that contains phthalocyanine, a photosensitizer, and streptavidin, which binds to biotinylated CHO derived human Fc. When FcRn-His and the biotinylated human Fc bind together, they bring the acceptor and donor beads into close proximity. When laser light is applied to this complex, ambient oxygen is converted to singlet oxygen by the donor bead. If the beads are in close proximity, an energy transfer to the acceptor bead occurs, resulting in light production (luminescence), which is measured in a plate reader equipped for AlphaScreen® signal detection.

When an antibody is present at sufficient concentrations to inhibit the binding of FcRn-His to the biotinylated human Fc domain, a dose dependent decrease in emission at 570 nm is observed. The test sample binding relative to the antibody reference standard is determined and reported as % relative binding and can be used to demonstrate the integrity of the Fc domain of the antibody. It is contemplated that compositions having the PARG (SEQ ID NO: 8) C-terminal variant will have a similar or better dose response curve than the wild type antibody.

The results are shown in FIG. 4. It was observed that both wild type romosozumab and PARG (SEQ ID NO: 8) C-terminal variant romosozumab bound FcRn similarly and FcRn binding was not affected by the PARG (SEQ ID NO: 8) mutation.

Example 8—FcγRIIa Binding

FcγRIIa is an activating Fc receptor expressed on monocytes, certain dendritic cells, neutrophils, B cells, platelets and NK cells. FcγRIIa (CD32a) is the most widely distributed FcγR with two extracellular Ig-like domains and low binding affinity for monomeric IgG. There are two common allelic variants in humans that are known to exist for FcγRIIa, expressing either histidine or arginine at position 131 (131H and 131R, respectively).

A competitive binding assay was developed to assess the binding of wild-type romosozumab and romosozumab PARG (SEQ ID NO: 8) C-terminal variant to FcγRIIa (131H). The FcγRIIa (131H) binding assay is a bead-based amplified luminescent proximity homogeneous assay (AlphaScreen® binding assay (PerkinElmer, San Jose, CA) that detects bimolecular interactions. The assay contains 2 bead types, an acceptor bead and a donor bead. The acceptor beads contain the fluorophore europium chelate and are coated with a hydrogel that contains glutathione, which binds recombinant human FcγRIIa (131H)-glutathione-S-transferase (FcγRIIa (131H)-GST). The donor beads are coated with a hydrogel that contains phthalocyanine, a photosensitizer, and streptavidin, which binds to biotinylated human IgG1. When FcγRIIa (131H)-GST and the biotinylated human IgG1 bind together, they bring the acceptor and donor beads into proximity. When a laser is applied to this complex, ambient oxygen is converted to singlet oxygen by the donor bead. When the acceptor and donor beads are near, the singlet oxygen diffuses within the acceptor beads resulting in light production (luminescence), which is measured in a plate reader equipped for luminescence signal detection.

When antibody is present at sufficient concentrations to inhibit the binding of FcγRIIa (131H)-GST to the biotinylated human IgG1, a dose-dependent decrease in emission at 570 nm is measured. The test sample binding relative to the antibody reference standard is determined and reported as % relative binding and can be used to demonstrate the integrity of the Fc domain of the antibody. The results are shown in FIG. 5. It was observed that the relative binding of PARG (SEQ ID NO: 8) C-terminal variant romosozumab to FcγRIIa (131H) was much higher than wild-type romosozumab.

Example 9—Mouse Pharmacokinetic Study

To evaluate in vivo drug exposure and bioavailability, a single dose pharmacokinetic study in mice is performed. Romosozumab PARG (SEQ ID NO: 8) C-terminal variant is injected either intravenously (via tail vein) or subcutaneously at a dose of 1 mg/kg. Using nine animals per group, staggered sampling permits collection of data at a large number of time points without exceeding the maximum volume of blood that can be drawn from an individual animal. At each time point, 0.05 ml of blood is drawn. Animals 1 to 3 are sampled at 0.083, 24, 96 and 192 hours post-dose. Animals 4-6 are sampled at 1, 48, 168 and 240 hours. Animals 7-9 are sampled at 6, 72 and 192 hours. Serum is collected from the whole blood sample and test article concentration is determined by a binding immunoassay such as an ELISA (Enzyme-Linked ImmunoSorbant Assay). Changes in test article concentration over time can be used to calculate pharmacokinetic parameters via two compartment analysis. Parameters of interest include, but not limited to, area under the plasma concentration-time curve (AUC), half-life ($t_{1/2}$) and clearance (CL) for each dose group. Bioavailability can be determined as the ratio of AUC for the subcutaneous dose to the AUC for the intravenous dose.

---

What is claimed is:

1. An antibody that specifically binds to sclerostin of SEQ ID NO: 1 and comprises a set of six CDRs set forth in SEQ ID NOs: 2-7, wherein the antibody comprises a heavy chain comprising the amino acid sequence Pro-Ala-Arg-Gly (SEQ ID NO: 8) at the C-terminus of the heavy chain, wherein the antibody comprises the light chain amino acid sequence set forth in SEQ ID NO: 12 and heavy chain amino acid sequence set forth in SEQ ID NO: 13 or SEQ ID NO: 14.

2. The antibody of claim 1, wherein the C-terminus of the heavy chain is amidated.

3. The antibody of claim 1, wherein the C-terminus of both heavy chains comprises the amino acid sequence Pro-Ala-Arg-Gly (SEQ ID NO: 8).

4. The antibody of claim 1, wherein the C-terminus of both heavy chains is amidated.

5. The antibody of claim 1, wherein the antibody comprises a sequence of amino acids comprising Pro-Ala-Arg-Gly-Lys (SEQ ID NO: 11) at the C-terminus of a heavy chain.

6. The antibody of claim 5, comprising the light chain amino acid sequence set forth in SEQ ID NO: 12 and the heavy chain amino acid sequence set forth in SEQ ID NO: 14.

7. A pharmaceutical composition comprising a population of antibodies of claim 1 and a pharmaceutically acceptable carrier.

8. The pharmaceutical composition of claim 7, wherein less than about 35% of the population of antibodies comprise heavy chains that are not amidated.

9. The pharmaceutical composition of claim 7, wherein about 33% of the population of antibodies are not amidated, about 33% of the population of antibodies comprise one amidated heavy chain, and about 33% of the population of antibodies comprise two amidated heavy chains.

10. The pharmaceutical composition of claim 7 comprising a calcium salt, an acetate buffer, a polyol and a surfactant.

11. The pharmaceutical composition of claim 7, further comprising 55 mM acetate, 13 mm calcium, 6.0% (w/v) sucrose, 0.006% (w/v) polysorbate 20, pH 5.2.

12. A method of increasing bone mineral density in a subject in need thereof comprising administering the composition of claim 7 to the subject in an amount effective to increase bone mineral density in the subject.

13. A pharmaceutical composition comprising a mixture of antibodies that specifically bind to sclerostin of SEQ ID NO: 1 and a pharmaceutically acceptable carrier;
    wherein about 3-5% of the antibodies in the composition are a population of antibodies of claim 1.

14. The pharmaceutical composition of claim 13, wherein all or part of the population of antibodies comprise a single heavy chain comprising a C-terminal Pro-Ala-Arg-Gly (SEQ ID NO: 8) sequence.

15. The pharmaceutical composition of claim 13, wherein all or part of the population of antibodies comprise a heavy chain comprising a C-terminal Pro-Ala-Arg-Gly (SEQ ID NO: 8) sequence that is amidated.

16. The pharmaceutical composition of claim 15, wherein less than about 35% of the population of antibodies is singly amidated.

17. The pharmaceutical composition of claim 13, wherein all or part of the population of antibodies comprise a C-terminal Pro-Ala-Arg-Gly (SEQ ID NO: 8) sequence in both heavy chains.

18. The pharmaceutical composition of claim 17, wherein all or part of the population of antibodies comprising two heavy chains comprising a C-terminal Pro-Ala-Arg-Gly (SEQ ID NO: 8) sequence are amidated on both heavy chains.

19. The pharmaceutical composition of claim 18, wherein less than about 35% of the population of antibodies are amidated on both heavy chains.

* * * * *